US010207170B2

(12) United States Patent
Penn et al.

(10) Patent No.: US 10,207,170 B2
(45) Date of Patent: Feb. 19, 2019

(54) COMBINING STATISTICALLY DETERMINED CAPABILITIES OF A GOLFER WITH GOLF COURSE DATA TO AID SHOT SELECTION

(71) Applicant: PERCENTAGEPLAY GOLF, LLC, Park Ridge, IL (US)

(72) Inventors: Kurt Penn, Park Ridge, IL (US); Guillermo Rosales, Jr., Wheeling, IL (US)

(73) Assignee: PERCENTAGEPLAY GOLF, LLC, Park Ridge, IL (US)

( * ) Notice: Subject to any disclaimer, the term of this patent is extended or adjusted under 35 U.S.C. 154(b) by 142 days.

(21) Appl. No.: 14/325,860

(22) Filed: Jul. 8, 2014

(65) Prior Publication Data

US 2015/0126308 A1   May 7, 2015

Related U.S. Application Data

(60) Provisional application No. 61/900,650, filed on Nov. 6, 2013, provisional application No. 61/929,705, filed on Jan. 21, 2014.

(51) Int. Cl.
A63B 69/36  (2006.01)
G06F 19/00  (2018.01)
G06Q 10/06  (2012.01)
G06K 9/00   (2006.01)

(52) U.S. Cl.
CPC .......... *A63B 69/36* (2013.01); *G06F 19/3481* (2013.01); *G06K 9/00342* (2013.01); *G06Q 10/0639* (2013.01); *A63B 2069/3605* (2013.01)

(58) Field of Classification Search
CPC ................. A63B 69/36; A63B 2069/3605
See application file for complete search history.

(56) References Cited

U.S. PATENT DOCUMENTS

| 5,245,537 A | 9/1993 | Barber |
| 5,283,732 A | 2/1994 | Mauritz |
| 5,294,110 A | 3/1994 | Jenkins et al. |
| 5,319,548 A * | 6/1994 | Germain ............... A63B 71/06 273/DIG. 26 |
| 5,507,485 A | 4/1996 | Fisher |
| 5,740,077 A | 4/1998 | Reeves |

(Continued)

FOREIGN PATENT DOCUMENTS

WO    WO 9404982 A1 *  3/1994   ......... A63B 71/0669

OTHER PUBLICATIONS

International Search Report and Written Opinion dated Feb. 5, 2015, relating to International Application No. PCT/US2014/061891.

*Primary Examiner* — David Duffy
(74) *Attorney, Agent, or Firm* — Barnes & Thornburg LLP; Mark J. Nahnsen

(57) ABSTRACT

A system for aiding the selection of a golf shot by a golfer on a hole of a golf course, comprising means for retrieving statistics indicative of past performances by the golfer for each of a plurality of golf club types, means for retrieving data regarding the hole of the golf course, means for analyzing the retrieved statistics in concert with the data regarding the hole of the golf course, means for selecting one of the golf club types as the statistically preferred golf club type for the golf shot, and means for displaying the selected golf club type to the golfer.

12 Claims, 12 Drawing Sheets

(56) References Cited

U.S. PATENT DOCUMENTS

| | | |
|---|---|---|
| 5,779,566 A | 7/1998 | Wilens |
| 5,810,680 A * | 9/1998 | Lobb ................. A63B 24/0021 473/407 |
| 5,882,269 A | 3/1999 | Lewis |
| 6,456,938 B1 | 9/2002 | Barnard |
| 7,014,576 B1 | 3/2006 | Posey |
| 7,118,498 B2 | 10/2006 | Meadows et al. |
| 7,121,962 B2 | 10/2006 | Reeves |
| 7,175,177 B2 | 2/2007 | Meifu et al. |
| 7,273,427 B2 | 9/2007 | Inoue et al. |
| 8,113,967 B1 * | 2/2012 | Seluga ............... A63B 24/0021 473/131 |
| 8,172,702 B2 | 5/2012 | Meadows et al. |
| 8,202,148 B2 | 6/2012 | Young |
| 8,221,269 B2 | 7/2012 | Meadows et al. |
| 8,246,050 B2 * | 8/2012 | Do ....................... A63D 15/006 273/317 |
| 8,364,293 B2 | 1/2013 | Doherty et al. |
| 8,435,140 B1 * | 5/2013 | Seluga ............... A63B 24/0021 473/131 |
| 8,529,380 B1 | 9/2013 | Hubenthal et al. |
| 2002/0038178 A1 | 3/2002 | Talkenberg ........ A63B 24/0021 701/532 |
| 2002/0038515 A1 | 4/2002 | Bradstock |
| 2002/0161461 A1 * | 10/2002 | Lobb ................. A63B 24/0021 700/91 |
| 2005/0032592 A1 | 2/2005 | Stec |
| 2005/0101415 A1 * | 5/2005 | Sweeney ........... A63B 24/0021 473/407 |
| 2005/0221905 A1 * | 10/2005 | Dunne .................. A63B 57/00 473/131 |
| 2005/0227791 A1 * | 10/2005 | McCreary .......... A63B 69/3658 473/407 |
| 2006/0030422 A1 | 2/2006 | Rankin et al. |
| 2007/0065791 A1 | 3/2007 | Rose |
| 2007/0129178 A1 | 6/2007 | Reeves |
| 2007/0129179 A1 | 6/2007 | Soto |
| 2008/0058125 A1 * | 3/2008 | Nguyen ................. A63B 57/00 473/407 |
| 2010/0009780 A1 * | 1/2010 | Doherty ............. A63B 24/0021 473/407 |
| 2010/0160089 A1 | 6/2010 | Lin et al. |
| 2010/0178994 A1 * | 7/2010 | Do ....................... A63D 15/006 473/2 |
| 2010/0179005 A1 | 7/2010 | Meadows et al. |
| 2010/0331120 A1 | 12/2010 | Galindo |
| 2011/0183779 A1 | 7/2011 | Baker et al. |
| 2011/0230273 A1 * | 9/2011 | Niegowski ........... A43B 3/0005 473/199 |
| 2011/0230274 A1 * | 9/2011 | Lafortune ............ A43B 3/0005 473/217 |
| 2011/0230985 A1 * | 9/2011 | Niegowski ........... A43B 3/0005 700/91 |
| 2011/0230986 A1 * | 9/2011 | Lafortune ............ A43B 3/0005 700/93 |
| 2011/0237358 A1 | 9/2011 | Carpenter |
| 2012/0309553 A1 | 12/2012 | Koudele et al. |
| 2013/0041487 A1 | 2/2013 | Messner et al. |
| 2013/0085018 A1 * | 4/2013 | Jensen .................. A63B 57/00 473/404 |
| 2013/0116061 A1 | 5/2013 | Zhao |
| 2013/0166199 A1 | 6/2013 | Reeves |
| 2013/0184094 A1 | 7/2013 | Rauchholz |

* cited by examiner

COMBINING STATISTICALLY DETERMINED CAPABILITIES OF A GOLFER WITH GOLF COURSE DATA TO AID SHOT SELECTION

CROSS REFERENCE TO RELATED APPLICATIONS

This application claims the benefit of priority under 35 U.S.C. § 119(e) to U.S. Provisional Patent Application Ser. No. 61/900,650, filed Nov. 6, 2013, and U.S. Provisional Patent Application Ser. No. 61/929,705, filed Jan. 21, 2014, the disclosures of which are hereby incorporated by reference in their entireties.

FIELD

The present disclosure relates to systems, components, and methodologies for aiding the selection of a golf shot by a golfer on a hole of a golf course.

BACKGROUND

A golfer will typically select a golf shot by selecting a golf club type and a line of aim. Most golfers will make such a selection based on their general ideas regarding how they perform with different golf club types, including how far they can hit a golf ball with those golf club types and what direction the golf ball's trajectory tends to follow when they aim in a particular direction with those golf club types. For example, a golfer may know that he can hit a golf ball using a given golf club type about 150 yards. The golfer may also apply rough heuristics to determine how far he can hit the golf ball using other golf club types—for example, by subtracting 10 yards for each consecutive iron golf club. However, golfers do not know their true, statistically-informed capabilities regarding how far the golfer can hit with each of the golf club types.

Similarly, golfers may have general ideas on the direction that a golf ball travels when the golfer uses a given golf club type. Rarely will a shot end up at its "visualized" location, e.g., 240 yards at the left-center of the fairway. However, golfers do not know the true, statistically-informed direction in which the golfer's golf shots typically travel.

Moreover, a golfer may not take into account the variance in the distance that he can achieve when hitting with different golf club types. While the golfer may believe he can hit a golf ball about 150 yards using a particular golf club type on average, this does not take into account whether the golfer consistently achieves about 150 yards on the one hand, or whether the golfer often undershoots and/or overshoots this distance by large amounts. Similarly, a golfer may not take into account the variance in the direction with which the golfer's shots typically travel.

Golfers sometimes rely on a caddie to analyze the course, the circumstances of the golfer's specific shot at hand, and the player's abilities with different golf club types in order to make a recommendation of a golf club type and line of aim for the player. The caddie may scout out the course before a tournament so that a course management plan can be developed for each of the holes, starting at the tee box at each hole. But even a caddie will generally not have precise and statistically-informed information about a golfer's capabilities.

Moreover, a decision for a particular shot should not just take into account the potential result of the current shot at hand, but should also consider subsequent shots such that the golfer selects a shot that will result in the lowest probable score for the entire hole. This is sometimes known as "Course Management," and is an important factor for a player to achieve the lowest possible score on any given course. This is why professional golfers sometimes select seemingly unconventional golf shots, such as using a fairway wood or an iron off the tee on long holes. But without the knowledge of probable outcomes of a golf shot with a given club and line of aim, the golfer may make sub-optimal decisions. These judgment errors will add strokes to the player's score in every round he plays.

There are numerous possible outcomes for a given shot at hand using a given golf club type, and each one of those possible outcomes gives rise to its own set of possible subsequent outcomes depending on how the golfer performs on subsequent shots. In order to identify a statistically-preferred golf shot, one should take into account these possible outcomes and their respective likelihoods. The number of possible outcomes and the computational complexity of identifying statistically-preferred golf shots based on their likelihoods is beyond the ability of most golfers, even if they had access to relevant statistics based upon which such computations could be performed.

Thus, to achieve the lowest statistically probable score for a hole, it is important for a golfer to know his statistical capabilities for each of his golf club types and to understand how a current golf shot selection can impact the score he can expect to achieve for the entire hole. Most golfers, however, do not have such information.

Accordingly, there is a need for improved systems, components, and methodologies to aid the selection of a golf shot by a golfer.

SUMMARY

According to the present disclosure, systems, components, and methodologies are provided for aiding the selection of a golf shot by a golfer on a hole of a golf course. The systems, components, and methodologies may combine data about a golf course and statistical data about the golfer's abilities to hit with various golf club types and allow the golfer to make a more informed decision about a particular golf shot at hand, as the golfer will know the probability of success and likely outcomes on the hole for the chosen shot. The systems, components, and methodologies iterate through a number of potential golf shot scenarios, taking into account statistically likely outcomes of subsequent shots, to provide the user with options for a golf shot that result in low statistically probable score from the golfer's location on a hole.

In illustrative embodiments, the systems, components, and methods aid the selection of a golf shot by a golfer on a hole of a golf course by retrieving statistics indicative of past performances by the golfer for each of a plurality of golf club types, retrieving data regarding the hole of the golf course, analyzing the retrieved statistics in concert with the data regarding the hole of the golf course, selecting one of the golf club types as the statistically preferred golf club type for the golf shot, and displaying the selected golf club type to the golfer.

Additional features of the present disclosure will become apparent to those skilled in the art upon consideration of illustrative embodiments exemplifying the best mode of carrying out the disclosure as presently perceived.

BRIEF DESCRIPTION OF THE DRAWINGS

The detailed description particularly refers to the accompanying figures in which:

FIG. 3 shows the display of confidence areas.

FIG. 4 shows regions demarcated by physical features of the golf course, and displays likelihoods that the golf shot will land within each of the regions.

DETAILED DESCRIPTION

The figures and descriptions provided herein may have been simplified to illustrate aspects that are relevant for a clear understanding of the described devices, systems, and methods, while eliminating, for the purpose of clarity, other aspects that may be found in typical devices, systems, and methods. Those of ordinary skill may recognize that other elements and/or operations may be desirable and/or necessary to implement the devices, systems, and methods described herein. Because such elements and operations are well known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Figure 1:
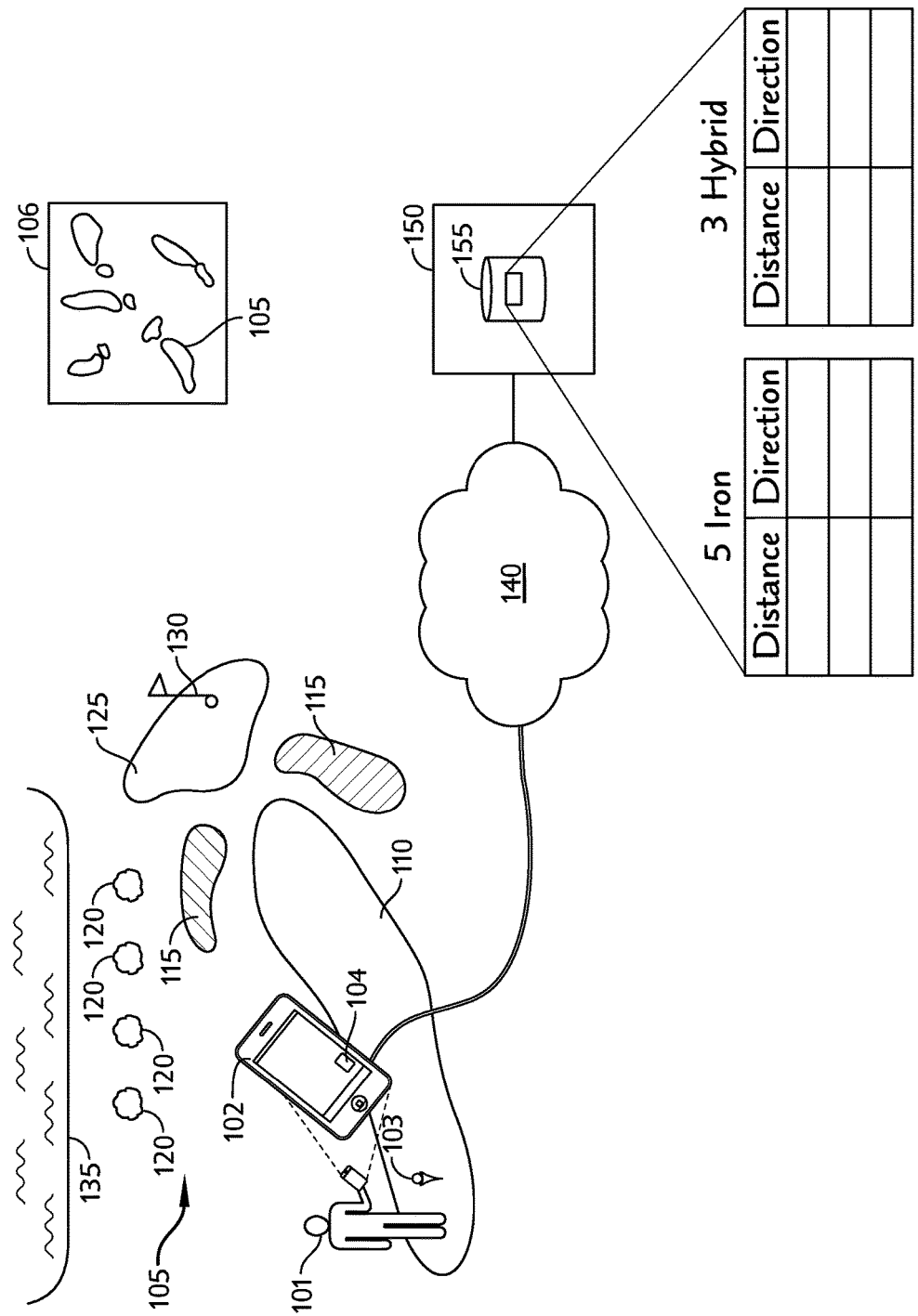
FIG. 1 is a diagram showing the operating environment for an exemplary system used by a golfer to aid in selection of a golf shot while on a golf course, in accordance with the present disclosure.

FIG. 1 is a diagram showing the operating environment for an exemplary system used by a golfer to aid in selection of a golf shot while on a golf course. FIG. 1 shows a golfer 101, a golf ball 103, and a hole generally indicated at 105 located on a golf course 106. The golfer 101 uses a mobile computing device 102 containing a software application 104 that aids in the selection of a golf shot. The mobile computing device 102 is connected through a network 140 to a database server 150 having a database 155.

By way of overview, the golfer 101 uses the software application 104 to obtain information, analysis, and recommendations regarding golf shot selection. The mobile computing device takes into account data regarding the position of the golfer 101 on the hole 105, data regarding the geography and physical features of the hole 105, and data regarding the golfer's past performance using different golf club types. According to one illustrative embodiment, the mobile computing device obtains information regarding the hole 105 and data regarding the golfer's past performance from the database 155. The statistical data about the capabilities of golfer 101 are collected by measurements taken at a driving range, inside hitting bays, on the golf course 106, or at other locations, and are stored in the database 155. The mobile computing device 102 performs statistical computations based on the data and recommends to the golfer 101 a statistically preferred golf shot. According to illustrative embodiments, the recommendation for the golf shot includes a recommendation on a golf club type and a recommendation for a target directional line. The mobile computing device 102 displays its recommendation to the golfer 101, along with additional information regarding the statistical likelihood of various outcomes of the golf shot should the golfer 101 adopt the recommendation. The mobile computing device 102 further displays alternative golf club types and/or alternative target directional lines, which the golfer 101 can select to learn about statistical likelihoods of various outcomes should the golfer 101 elect to use one of the alternatives.

Continuing with the overview, the software application 104 may recommend a golf shot (including a golf club type and a target directional line) that would result in the lowest expected score from the current location of the golfer 101 on the hole 105. By combining data about the course with statistical data about the golfer's capabilities, the software application 104 can calculate probable outcomes of various golf shots from the current location of the golfer 101 and potential locations from which the golfer 101 will take subsequent shots. The software application 104 computes outcomes and their likelihoods for a number of scenarios, compares the resulting computations, and provides the user with the statistically preferred golf shot that results in the lowest statistically probable score from that location. The system then provides data to the user about the statistically probable result of the statistically preferred golf shot, confidence intervals associated with different outcomes that may result from the shot, and a statistically probable total number of strokes from that particular location until the hole is finished.

In more detail with respect to FIG. 1, the golfer 101 may be any individual attempting to select a golf shot for the purpose of hitting the golf ball 103. While the golfer 101 may be the actual individual hitting the golf ball 103, it should be understood that the systems disclosed herein can be used not just by the golfer 101, but also by other individuals, including a caddie or a sports commentator analyzing the performance of the golfer 101. In such a situation, the screen displays set forth below would be provided as a television graphic for distribution to over telecommunications systems to home television sets, rather than on mobile computing device 102.

The golfer 101 may want to select the golf shot that will result in the lowest expected score for the hole 105. The selection of the golf shot may include selecting a golf club type and selecting a target directional line. The golf club types available to the golfer are generally known, and may include woods, irons, hybrids, putters, and chippers. The line of aim refers to the line that the golfer 101 attempts to follow when striking the golf ball 103, and may be different than the trajectory that the golf ball 103 actually follows after being struck. For example, the golfer 101 may want a line of aim that proceeds to the left of a target directional line if that golfer's shots using a particular golf club type tend to follow right-leaning trajectories as compared to where the golfer 101 aims.

According to the illustrative embodiment, the hole 105 includes a fairway 110, bunkers 115, a water hazard 135, tree hazards 120, a green 125, and a physical hole 130. The physical hole 130 should not be confused with the hole 105. The hole 105 refers to one of the discrete units of play on the full golf course, for which a typical golf course may have 9 or 18. The physical hole 130 refers to the orifice disposed within the green 125, often containing a cup (not shown), into which the golfer 101 is attempting to place the ball 103. For clarity, this specification will distinguish between a "hole" 105 and a "physical hole" 130.

According to this illustrative embodiment, the mobile computing device 102 is a mobile smartphone, but in other embodiments may be implemented as a tablet, a PDA, a multimedia computer, a laptop, a Golf GPS Device, and the like. Additional details regarding the hardware components of mobile computing device 102 will be discussed further below in connection with FIG. 11. For present purposes, the mobile device 100 includes an operating system which may be selected from among, but not limited to, Apple's iOS line of operating systems, the Android line of operating systems, the Windows Mobile or Windows Phone line of operating systems, or BlackBerry operating systems. Mobile device 102 also includes a third party software application 104, depicted in FIG. 1 by way of an icon on the screen display of mobile device 102. The software application 104 can either be natively provided on the mobile device 102 or can be downloaded, such as through distribution platforms like the Apple App Store, Google Play, Windows Phone Store or BlackBerry App World. According to this illustrative embodiment, the functionality for aiding the golfer 101 select a golf shot is provided by the software application 104 in concert with hardware provided on the mobile device 102, including processors and memory, as will be discussed in more detail in connection with FIG. 11.

Database server 150 and database 155 may be implemented using any known database environment, such as Oracle, DB2, or SQL Server. Database 155 may be a relational database. Although the database 155 is depicted as being housed on a separate database server 150, it should be understood that in certain embodiments, the mobile computing device 102 contains the database 155 within internal storage.

The software application 104 communicates with the database 155 through network 140. Mobile device 102 may include network connectivity, such as cellular network connectivity and/or wireless local area networking capabilities (i.e., "WiFi"), which enables software applications installed on mobile device 102 to connect to the network 140. The network 140 may include any type of communication network, such as a cellular communication network, including but not limited to a second Generation (2G) network, a 2.5 Generation network, a third Generation (3G) network utilizing Global System for Mobile Communications (GSM), a fourth Generation (4G) network, Wideband Code Division Multiplex Access (WCDMA), Code Division Multiplex Access (CDMA), Time Division Multiplex Access (TDMA), General Packet Radio Services (GPRS), or Universal Mobile Telephone System (UMTS). Network 140 can also be implemented as a combination of two or more technologies i.e., a hybrid network. Further, network 140 may include generic Internet access using any transport methods.

As explained, the database 155 contains information regarding the geography of the golf course 106 and, in particular, the hole 105, including the location of the fairway 110, the bunkers 115, the water hazard 135, the tree hazards 120, the green 125, and the physical hole 130. This information may be provided by a manager of the golf course 106, by a third party service (which may include the provider of the software application 104) that collects information on the golf course 106 and uploads it to the database 155, or may be manually inputted into the database 155 by the golfer 101 through a user interface presented by the software application 104.

Figure 2:
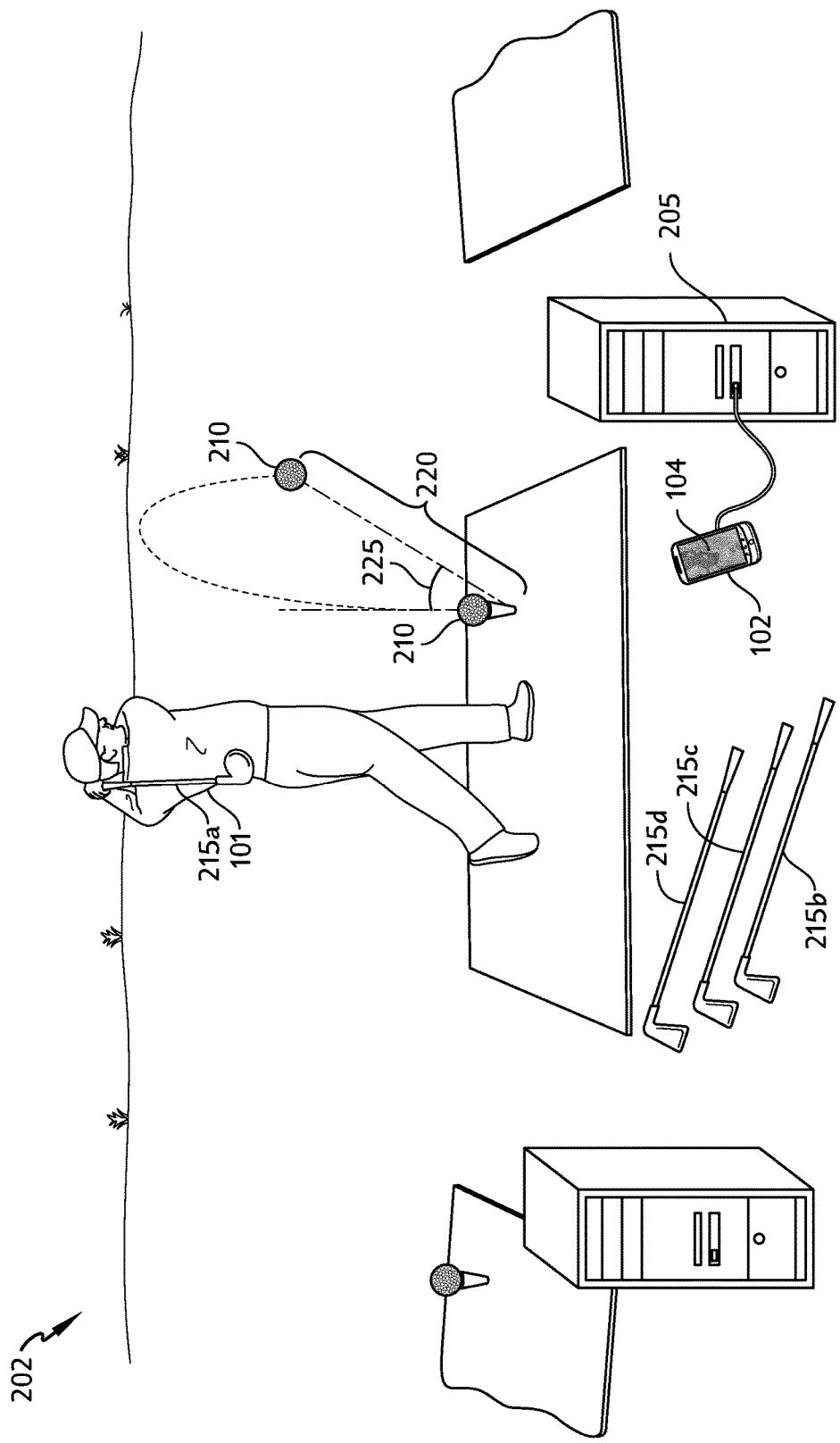
FIG. 2 is a block diagram showing the operating environment for an exemplary system used by a golfer to collect statistics about the golfer's past performances, in accordance with the present disclosure.

The database 155 also contains statistical data regarding the past performances of golfer 101. FIG. 2 is a diagram showing the operating environment for an exemplary system used by a golfer 101 to collect statistics about the golfer's past performances. FIG. 2 shows the golfer 101 at a driving range or hitting bay 202. The golfer 101 uses a golf club type 215a to hit the ball 210. The driving range or hitting bay includes equipment that tracks the trajectory of the ball 210, including a distance 220 and a directional orientation 225 of its trajectory. Exemplary systems that can provide tracking information of this type includes that provided by Trackman® of Denmark. The distance 220 and directional orientation 225 are collected in a server 205. The golfer 101 connects his mobile computing device 102 to the server 205 and invokes the software application 104. The software application 104 downloads the information regarding the golf club type 215a, the distance 220, and the directional orientation 225 to an internal storage of the mobile computing device (to be described in connection with FIG. 11), and transmits that information to the database 155 over the network 140. The database 155 stores the information in an appropriate database table, as depicted in FIG. 1, showing an exemplary "5 iron" database table and an exemplary "3 hybrid" database table.

The golfer 101 continues to hit golf ball 210 and/or other golf balls using golf club type 215a, as well as other golf club types 215b, 215c, and 215d. In this illustrative embodiment, golf club type 215a is a driver, golf club type 215b is a 2 iron, golf club type 215c is a 3 wood, and golf club type 215d is a 3 hybrid. Generally, the golfer 101 will hit balls using all golf club types that he intends to use when on golf course 106. Other examples of golf club types for which data can be stored in the database 155 might include "half wedges," a "punch 5-iron," or a "choked-down 7-iron."

In time, the database 155 will store a sufficiently sized sample set of statistics to reflect the capabilities of the golfer 101 with respect to distance 220 and direction 225 for each golf club type 215a-d.

In certain embodiments, data regarding the past performances of the golfer 101 are collected as the golfer plays on the golf course 106 and transmitted to the database 155. The data thus collected can be available for immediate analysis and use by the software application 104.

In other illustrative embodiments, the golfer 101 manually enters data into the software application 104. The data that the golfer 101 enters can include a sequence of distance and direction measurements for golf club types 215a-d. Alternatively, the golfer 101 can manually compute summary statistics regarding distance and direction for golf club types 215a-d, such as an average and/or a variance for both distance and direction, and enter the summary statistics into the software application 104 without entering individual, per-shot distance and direction measurements. In still other embodiments, the golfer 101 enters measurements and/or summary statistics through a computer interface different from that provided by the mobile computing device 102, such as through a home personal computer (not shown). The measurements and/or statistics entered by the golfer 101 are then transmitted to the database 155 over the network 140, to which the home personal computer may be connected.

Figure 3:
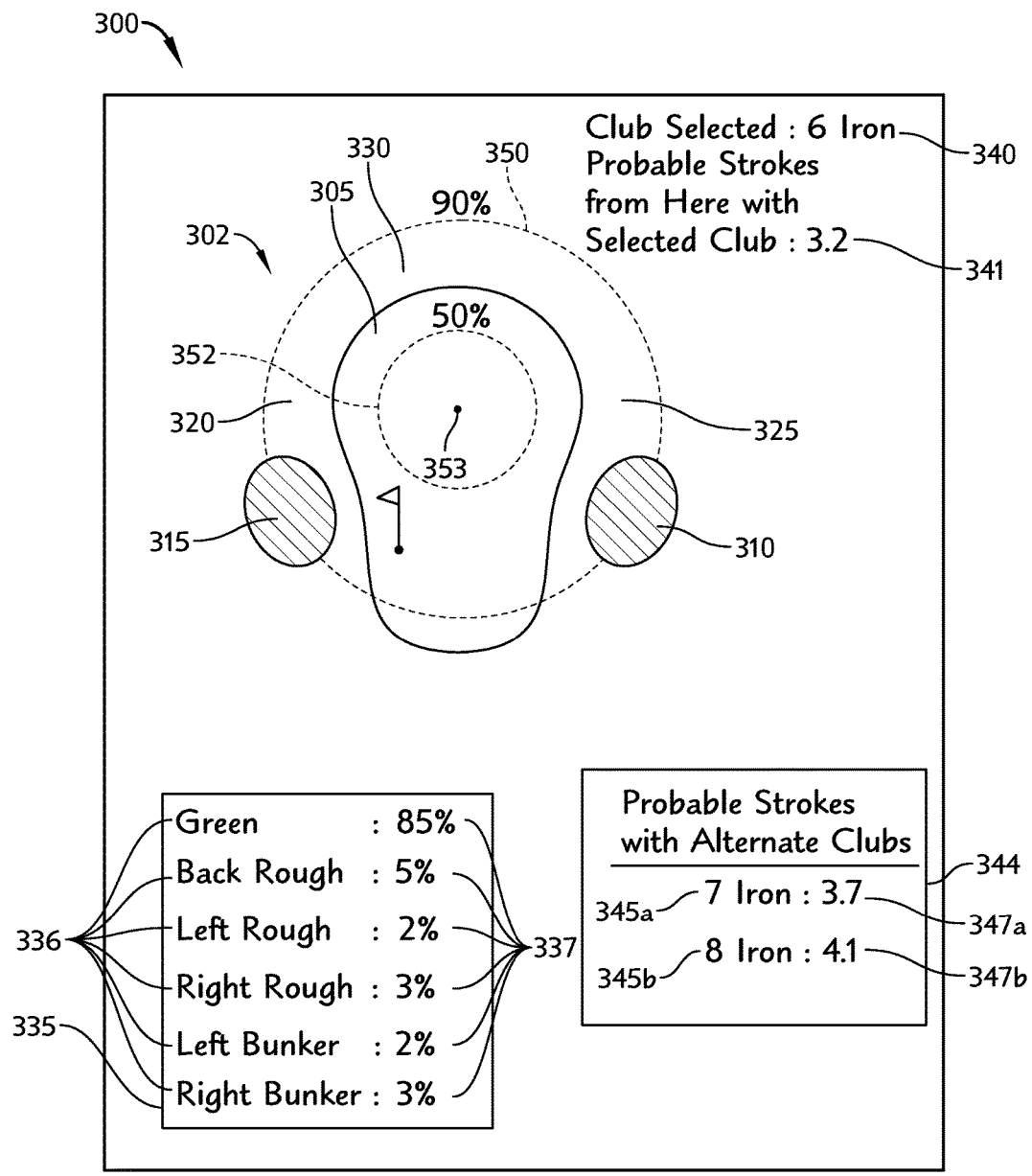
FIG. 3 is an exemplary screen display presented by a system to a golfer for the purpose of providing information, analysis, and recommendations regarding golf shot selection, in accordance with the present disclosure. In particular.

FIG. 3 is an exemplary screen display 300 presented by a system to a golfer 101 for the purpose of providing information, analysis, recommendations, and assistance regarding golf shot selection. As will be explained in connection with FIG. 11, in certain embodiments, the screen display 300 is a touch screen or stylus-driven touch sensitive display provided by the mobile computing device 102. The screen display 300 shows a graphical depiction of a portion of a hole 302 similar to the hole 105 described above in connection with FIG. 1. The screen display 300 includes graphical depictions of a green 305, a right rough 325, a left rough 320, a back rough 330, a right bunker 310, and a left bunker 315.

The screen display 300 is presented to the golfer 101 after the software application 104 determines a recommended golf shot. The screen display 300 shows the recommended golf club type 340 resulting in the lowest probable score for the golfer 101. Although the screen display 300 does not show a recommended line of aim, certain embodiments will include a recommended line of aim, as will be depicted in connection with screen displays discussed below. The manner by which the software application 104 processes data from database 155 and performs statistical computations to identify the recommended golf club type 340 and a recommended line of aim will be discussed in more detail below in connection with FIGS. 7-9.

The screen display 300 shows the recommended golf club type 340 by showing the text of the golf club type 340—in this case, "6 iron." The screen display 300 may, in addition or in the alternative, include a picture of the golf club type 340. The screen display 300 also shows the number of probable strokes 341 for completing the hole 305 that the software application 104 computed for the recommended golf club type 340.

The screen display 300 also shows an alternative golf club type box 344 showing first and second alternative golf club types 345a and 345b that were not recommended—in this example, a 7 iron and an 8 iron. As with the recommended golf club type 340, alternative golf club types, such as alternative golf club types 345a and 345b, can be displayed through text—in this example, "7 iron" and "8 iron"—and/or with pictures. For each of the alternative golf club types 345a and 345b, the screen display shows the number of probable strokes 347a and 347b, respectively, for completing the hole 305 as computed by the software application 104. Although two alternative golf club types 345a and 345b are shown by the screen display 300 in this illustrative embodiment, the screen display 300 could display just one alternative golf club type or several additional alternative golf club types.

The screen display shows an expected landing location 353, also referred to as a "nominal" or "mean" landing location, which generally provides the expected (or statistical average) landing location for the golf ball 103 if the golfer 101 were to use the recommended golf club type 340.

The screen display 300 also shows confidence areas surrounding the expected landing location 353. The screen display 300 shows a 90% confidence area 350, which is a boundary overlayed on the graphical depiction of the hole 302 and that reflects a confidence region or confidence interval. Specifically, the software application 104 has determined that there is a 90% likelihood that use of the recommended golf club type 340 will result in the golf ball 103 landing within the region of the hole 302 demarcated by the 90% confidence area 350. In other words, given the current state of play for the golfer 101, the golfer 101 using the golf club type 340 will land the golf ball 103 within the region demarcated by the 90% confidence area 350 approximately nine times out of ten.

The screen display 300 also shows a 50% confidence area 352. Here, the software application 104 has determined that there is a 50% likelihood that the golf shot recommended by the software application 104, using the recommended golf club type 340, will result in the golf ball 103 landing within the region of the hole 302 demarcated by the 50% confidence area 352. Although the screen display 300 shows a 90% confidence area 350 and a 50% confidence area 352, other confidence areas may be displayed, such as one or more of a 10% confidence area, a 20% confidence area, a 25% confidence area, a 30% confidence area, a 40% confidence area, a 50% confidence area, a 60% confidence area, a 70% confidence area, a 75% confidence area, and an 80% confidence area.

In this illustrative embodiment, the screen display 300 shows multiple confidence areas—the 90% confidence area 350 and the 50% confidence area 352—at the same time. In other illustrative embodiments, the screen display 300 shows just one confidence area. In still other embodiments, the golfer 101 may select one or more confidence areas that the screen display 300 will show. For example, the software application 104 may include a settings menu (not shown) listing multiple confidence areas and having a user interface selection mechanism, such as respective "radio buttons" or "check boxes," for selecting one or more of the confidence areas. Upon return to the screen display 300, the screen display 300 will show the selected confidence areas.

The screen display 300 also shows an event likelihood box 335 that displays statistical likelihoods 337 of certain events 336. The events 336 relate to possible landing locations for the golf ball 103 if the golfer 101 uses the recommended golf club type 340. Thus, one event 336 relates to the likelihood that the golf ball 103 will land in the green 305; one event 336 relates to the likelihood that the golf ball 103 will land in the left rough 320; one event 336 relates to the likelihood that the golf ball 103 will land in the right rough 325; one event 336 relates to the likelihood that the golf ball 103 will land in the back rough 330; one event 336 relates to the likelihood that the golf ball 103 will land in the left bunker 315; and one event 336 relates to the likelihood that the golf ball 103 will land in the right bunker 310. Associated with each of these events 336 is a respective statistical likelihood 337 computed by the software application 104.

In certain embodiments, the golfer 101 can select one of the alternative golf club types 345a or 345b, such as by touching the text "7 iron" or "8 iron" on the screen display 300, which as explained may be touch sensitive. Upon selecting one of the alternative golf club types 345a or 345b, the software application 104 will provide statistics for the alternative golf club type 345a or 345b and the screen display 300 will refresh to provide information regarding the alternative golf club type 345a or 345b. Thus, if the golfer 101 selects alternative golf club type 345a, the screen display will refresh the number of probable strokes 341, the 90% confidence area 350, the 50% confidence area 352, and the event likelihood box 335 as to reflect statistical computations by the software application 104 that are based on the alternative golf club type 345a. An exemplary refreshed screen display will be described in connection with FIG. 6, below.

Figure 4:
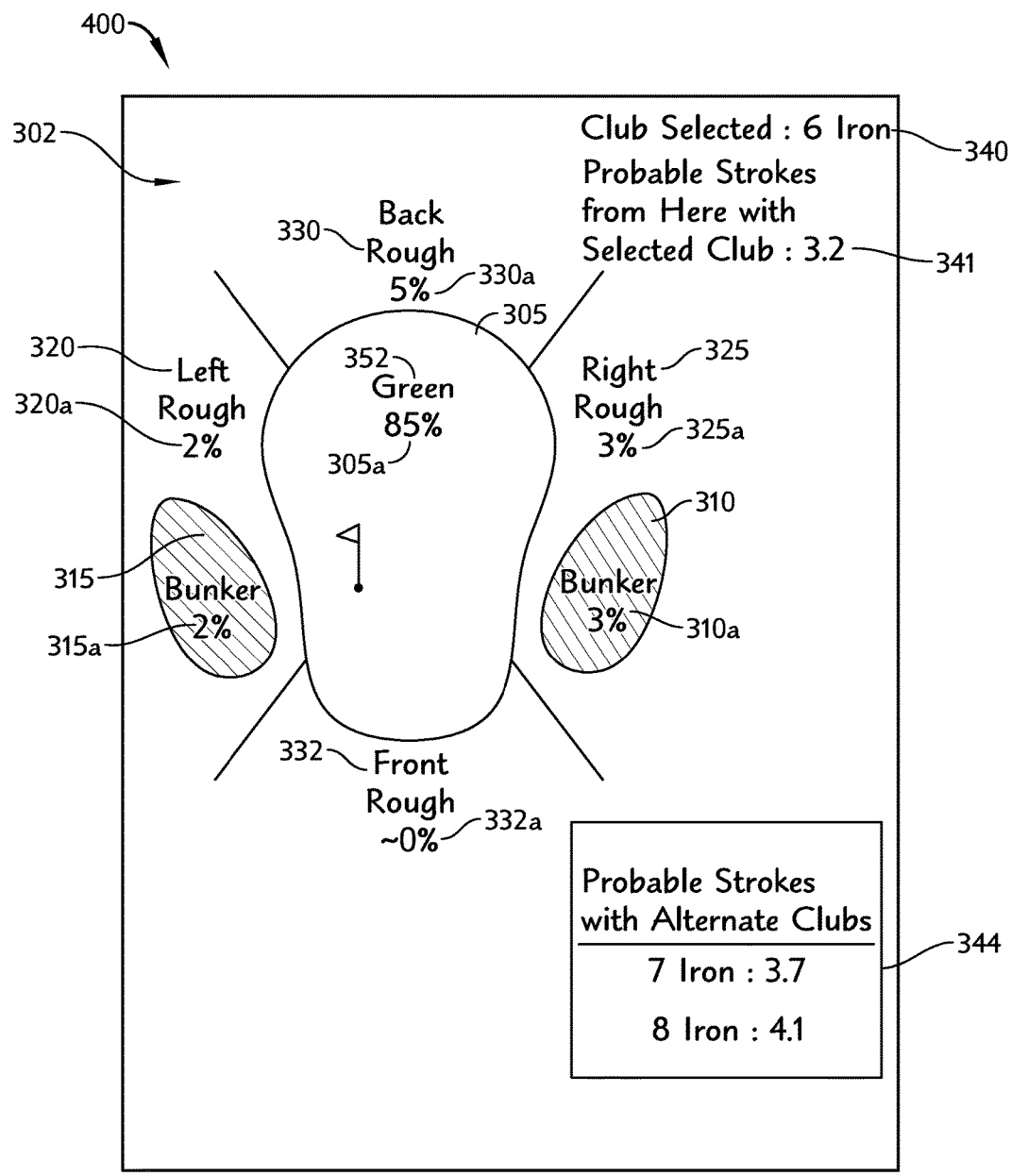
FIG. 4 is an exemplary screen display presented by a system to a golfer for the purpose of providing information, analysis, recommendations, and assistance regarding golf shot selection, in accordance with the present disclosure. In particular.

FIG. 4 is an exemplary screen display 400 presented by a system to a golfer 101 for the purpose of providing information, analysis, recommendations, and assistance regarding golf shot selection. The screen display 400 shows the portion of the hole 302 that was depicted in FIG. 3, including the green 305, right rough 325, left rough 320, back rough 330, right bunker 310, and left bunker 315. Also shown is a front rough 332. The screen display 400 also shows the recommended golf club type 340, the number of probable strokes 341, and the alternative golf club type box 344.

Whereas the screen display 300 of FIG. 3 showed a 90% confidence area 350 and a 50% confidence area 352, the screen display 400 shows statistical likelihoods that the golf ball 103 will land in regions of the hole 302 demarcated by physical features of the golf course. Thus, the screen display 400 shows a likelihood 305a that the golf ball 103 will land in the green 305, a likelihood 325a that the golf ball 103 will land in the right rough 325, a likelihood 320a that the golf ball 103 will land in the left rough 320, a likelihood 330a that the golf ball 103 will land in the back rough 330, a likelihood 310a that the golf ball 103 will land in the right bunker 310, a likelihood 315a that the golf ball 103 will land in the left bunker 315, and a likelihood 332a that the golf ball 103 will land in the front rough 332.

While the screen display 400 shows statistical likelihoods overlayed on a graphical depiction of a portion of the hole 302, other graphical, tabular, or other displays could be used to provide this calculated data to the golfer 101.

Figure 5:
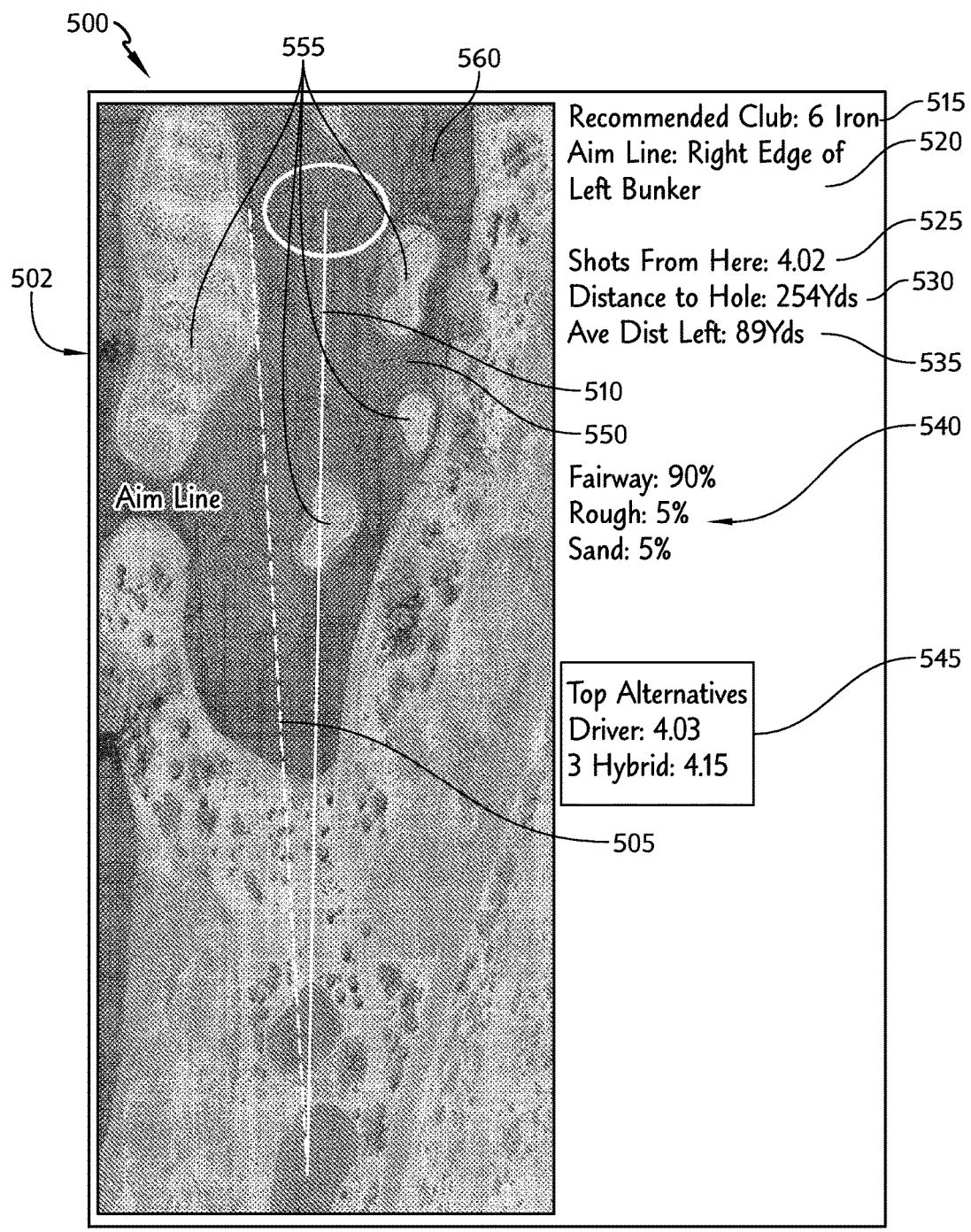
FIG. 5 is an exemplary screen display presented by a system to a golfer for providing information on a line of aim likely to result in the golf shot following a target directional line, in accordance with the present disclosure.

FIG. 5 is an exemplary screen display 500 presented by a system to a golfer 101 for providing information on a line of aim likely to result in the golf shot following a target directional line. The screen display 500 shows a portion of a hole 502, a line of aim (also referred to as an "aim line") 505, a target directional line 510, and a recommended golf club type 515. The software application 104 determines a target directional line 510 that is statistically likely to result in the lowest score for the golfer 101. The software application 104 uses direction measurements from past performances of the golfer 101 using the recommended golf club type 515 (collected using methodologies discussed in connection with FIG. 2) to determine where the golfer 101 should aim in order to maximize the likelihood that the golf ball 103 will have a trajectory following the target directional line 510. The screen display 500 shows the results of the software application's determination as the aim line 505. The screen display 500 may also include a textual description 520 of the aim line 505, but any user friendly mechanism for conveying information about the aim line 505 is within the scope of the present disclosure.

The target directional line 510 may be different from the aim line 505. For example, if the user normally hits a fade or a slice, the aim line 505 may be to the left of the target directional line 510, as shown in FIG. 5. Typically, the amount of fade or slice may vary from one golf club type to the next for any given golfer, so it is important for the golfer 101 to know the statistically preferred aim line 505 for a given target directional line 510 for the recommended golf club type 515.

The screen display 500 also shows a statistically expected number of shots 525 from the location of the golfer 101 to completion of the hole 502, a distance 530 from the location of the golfer 101 to a physical hole (not shown) on the hole 502, and an average distance expected to remain to a green (not shown) of the hole 502 should the golfer 101 use the recommended golf club type 515.

The screen display 500 also shows statistical likelihoods 540 of the golf ball 103 landing in certain physical regions of the hole 502 if the golfer 101 uses the recommended golf club type 515—in this illustrative embodiment, the screen display shows a 90% likelihood of landing in a fairway 550, a 5% likelihood of landing in sand 555, and a 5% likelihood of landing in a rough 560.

The screen display 500 also shows an alternative golf club type box 545, which in this illustrative embodiment shows two alternative golf club types (a "driver" and a "3 Hybrid") along with respective statistically expected strokes for completion of the hole 502 ("4.03" and "4.15") if the golfer 101 were to use one of the two alternative golf club types.

It should be understood that screen displays in accordance with the present disclosure may include any one or more of the following on a single screen display: confidence areas (such as the 90% confidence area 350 and the 50% confidence area 352 of FIG. 3); likelihoods associated with physical regions (such as the likelihoods 305a, 325a, 320a, 330a, 310a, 315a, and 332a shown in FIG. 4); an aim line (such as aim line 505 shown in FIG. 5), and a target directional line (such as target directional line 510 shown in FIG. 5).

Figure 6:
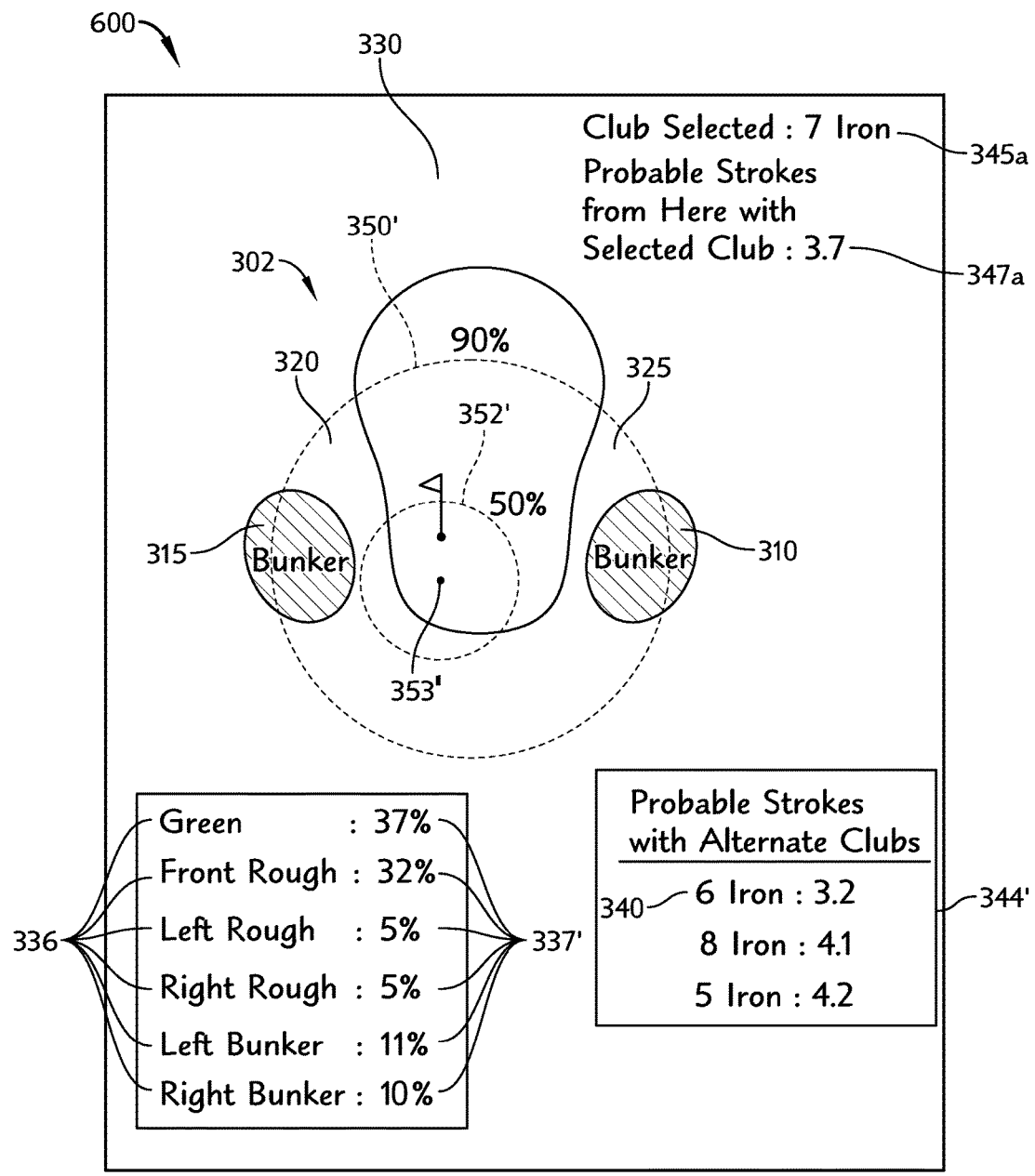
FIG. 6 is an exemplary screen display shown by a system in the circumstance in which a user is presented with a recommendation on a statistically preferred golf club type but selects an alternative golf club type, in accordance with the present disclosure.

FIG. 6 is an exemplary screen display shown by a system in the circumstance in which a user is presented with a recommendation on a statistically preferred golf club type but selects an alternative golf club type. As explained in connection with FIG. 3, the golfer 101 may select the alternative golf club type 345a, which in this example is a "7 iron". Upon selection of the alternative golf club type 345a, the screen display 300 refreshes as to show screen display 600. Thus, screen display 600 shows the same events 336 that were shown by screen display 300, but the statistical likelihoods 337 have been updated to reflect the computations of software application 104 based on the alternative golf club type 345a. The updated statistical likelihoods are indicated as 337' in FIG. 6.

The screen display 600 also shows a refreshed expected landing location 353', a refreshed 90% confidence area 350', and a refreshed 50% confidence area 352', all of which have been updated based on computations by software application 104 to account for the use of the alternative golf club type 345a rather than the recommended golf club type 340. The golf club type box 344 has also been refreshed, indicated in FIG. 6 as 344'. Now, the recommended golf club type 340 appears in the alternative golf club type box 344', and the golfer 101 can select the recommended golf club type 340 in order to revert back to screen display 300.

The software application 104 may also provide the golfer 101 with the ability to select whatever golf club type and target directional line he would want for each given shot, and the software application 104 may update the statistical computations for outcomes for the shot and for the hole. The golfer 101 would then have the ability to compare recommendations and alternatives that the system had provided for a variety of golf club types before making a final decision.

Figure 7A:
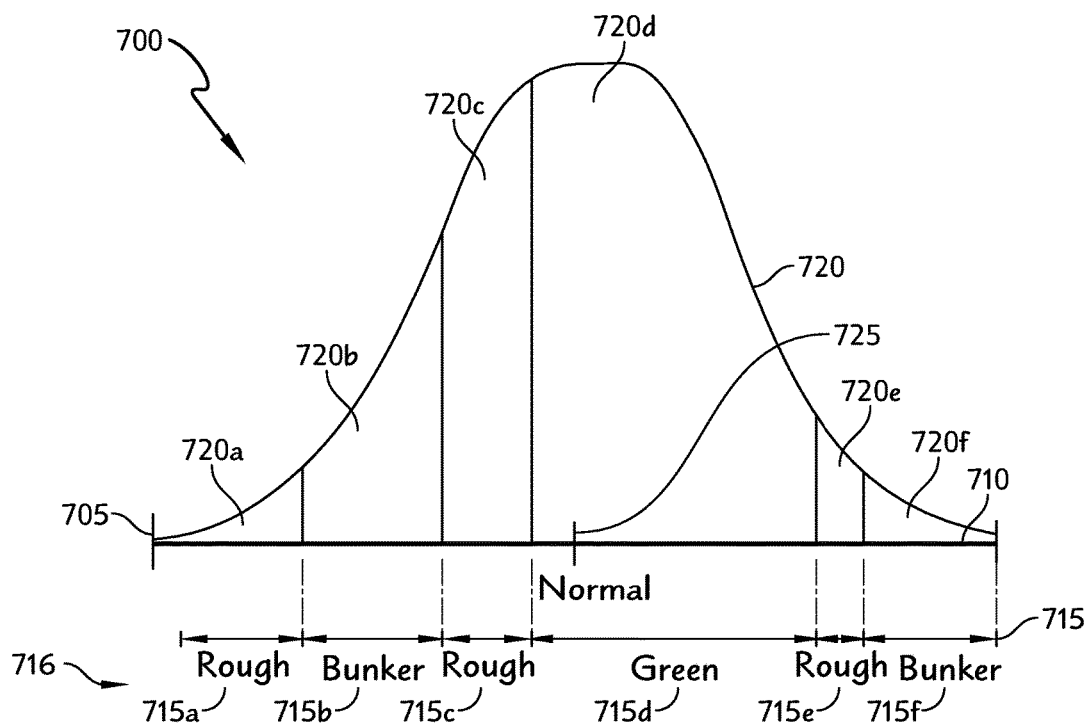
FIGS. 7A-B depict the manner by which an exemplary system computes statistical likelihoods by overlaying a statistical distribution over a programmatic representation of a golf course, in accordance with the present disclosure.
Figure 7B:
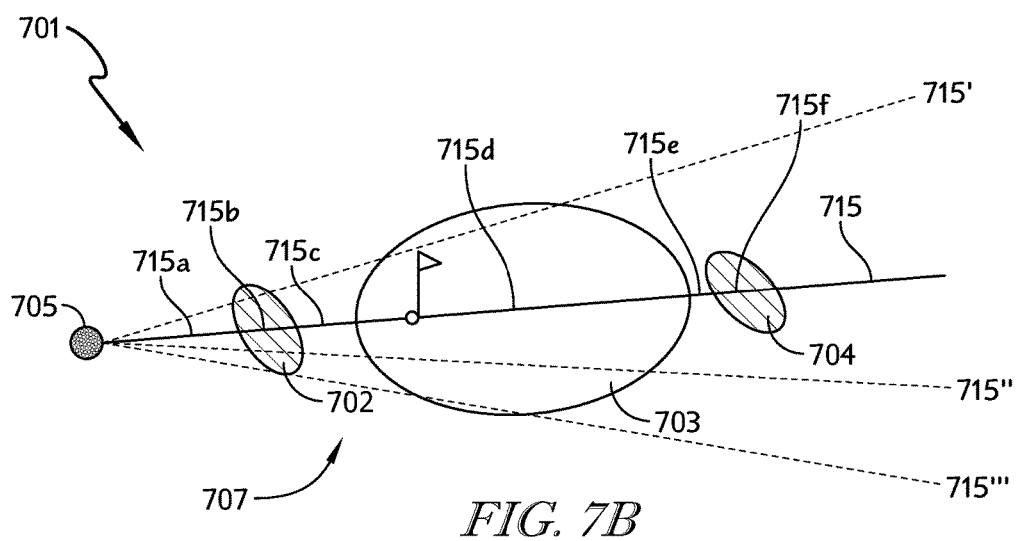

FIG. 7A is a diagram 700 depicting the manner by which the software system 104 computes statistical likelihoods. FIG. 7B depicts a hole 701 for which the diagram 700 corresponds.

Beginning first with FIG. 7B, a golfer 101 is shown at a location 705 of the hole 701. The hole 701 includes a rough generally indicated at 707, a first bunker 702, a green 703, and a second bunker 704. Also depicted on FIG. 7B is a directional line of analysis 715. As shown, the directional line of analysis 715 passes through a first portion of the rough 707 at the line segment 715*a*, passes through the first bunker 702 at the line segment 715*b*, passes through a second portion of the rough 707 at the line segment 715*c*, passes through the green 703 at the line segment 715*d*, passes through a third portion of the rough 707 at the line segment 715*e*, and passes through the second bunker 704 at a line segment 715*f*.

Generally, the software system 104 computes statistical likelihoods by overlaying a statistical distribution over a programmatic representation of a hole of a golf course. Specifically, FIG. 7A shows an axis 710, a statistical distribution 720, and a programmatic representation 716 of the portion of the hole 701 intersected by the directional line of analysis 715.

The software system 104 begins by identifying a golf club type of interest for which a statistical analysis will be performed. The software system 104 then identifies a directional line of analysis, which in this illustration is the directional line of analysis 715. The software system 104 next generates a programmatic representation 716 of the features of the hole 701 along the directional line of analysis 715. Thus, the programmatic representation 716 shows the line segments 715*a*, 715*b*, 715*c*, 715*d*, 715*e*, and 715*f*, all corresponding to features of the hole 701 intersected by the directional line of analysis 715, as described above.

The software system 104 aligns the programmatic representation 716 with the axis 710. On the axis 710, the software system 104 then generates a statistical distribution 720. The statistical distribution 720 represents a probability mass distribution for how far the golfer 101 is expected to hit the golf ball 103 using the golf club type currently under analysis. The software system 104 obtains the data for generating the statistical distribution 720 from the database 155. In certain embodiments, the software system 104 obtains past performance data regarding the distance with which the golfer 101 hit golf balls using the golf club type currently under analysis and applies known statistical techniques, such as regression analysis, to identify a statistical distribution 720 consistent with the past performance data. In certain embodiments, the software system 104 computes a mean and a standard deviation for the distance with which the golfer 101 can hit the golf ball 103 using the golf club type currently under analysis, and uses a normal distribution having the calculated mean and the calculated standard deviation as the statistical distribution 720. It would be expected that each golf club type would have a unique mean and a unique standard deviation for the golfer 101, with both the mean and the standard deviation increasing as golf club types increased from wedges to woods.

The software system plots the statistical distribution 720 on the axis 710, thus overlaying the statistical distribution 720 over the programmatic representation 716. The software system 104 can then calculate statistical likelihoods that the golf ball 103 will land in certain locations on the hole 701 along the directional line of analysis 715. Thus, the statistical likelihood that the golf ball 103 would land along line segment 715*a* is generally reflected by the area of the region 720*a* under the statistical distribution 720. The statistical likelihood that the golf ball 103 would land along line segment 715*b* is generally reflected by the area of the region 720*b* under the statistical distribution 720. The statistical likelihood that the golf ball 103 would land along line segment 715*c* is generally reflected by the area of the region 720*c* under the statistical distribution 720. The statistical likelihood that the golf ball 103 would land along line segment 715*d* is generally reflected by the area of the region 720*d* under the statistical distribution 720. The statistical likelihood that the golf ball 103 would land along line segment 715*e* is generally reflected by the area of the region 720*e* under the statistical distribution 720. The statistical likelihood that the golf ball 103 would land along line segment 715*e* is generally reflected by the area of the region 720*e* under the statistical distribution 720.

As the analysis described above was conditional on a particular directional line of analysis 715, the software system 104 may repeat the analysis described above for other directional lines of analysis 715', 715'', 715''', etc., weighting the results of the statistical computations for each directional line of analysis 715, 715', 715'', 715''', etc., based on a statistical likelihood that the golfer 101 will hit the golf ball 103 along a trajectory following the respective directional lines of analysis. Thus, the software system 104 rotates the directional line of analysis 715 to calculate statistical likelihoods of the possible results of a shot. The software system 104 obtains data regarding statistical likelihoods for the golfer 101 hitting the golf ball 103 along respective directional lines of analysis 715, 715', 715'', 715''', etc. by consulting the direction statistics for the golf club type currently under analysis stored in the database 155 described above in connection with FIG. 2. A decision on the number of directional lines of analysis 715, 715', 715'', 715''', etc. to analyze can be made by balancing the computational delay arising from adding additional directional lines of analysis 715, 715', 715'', 715''', etc., and the additional accuracy that results from using additional directional lines of analysis 715, 715', 715'', 715''', etc.

The description above is an exemplary methodology, and there could be any number of methods to provide calculations of statistical likelihoods, depending on factors including the calculation capabilities of the software system 104 or the mobile device 102, the type of course information stored in the software system 104 and/or database 155, the accuracy required/desired by the golfer 101, and other factors.

After computing statistical likelihoods as described above for a given golf club type, the software application 104 can repeat the computations for other golf club types in order to compare the results of the computations to identify a statistically preferred golf club type. For example, the software application 104 may select a golf club type that maximizes the likelihood that the golf shot will land in the green 703 or that minimizes the likelihood that the golf shot will land in the bunkers 702 and 704. However, in certain embodiments, the software application 104 selects a golf club type that results in the statistically lowest probable score for the hole 701 by considering outcomes associated with subsequent golf shots, as will be explained in connection with FIG. 9.

Figure 8:
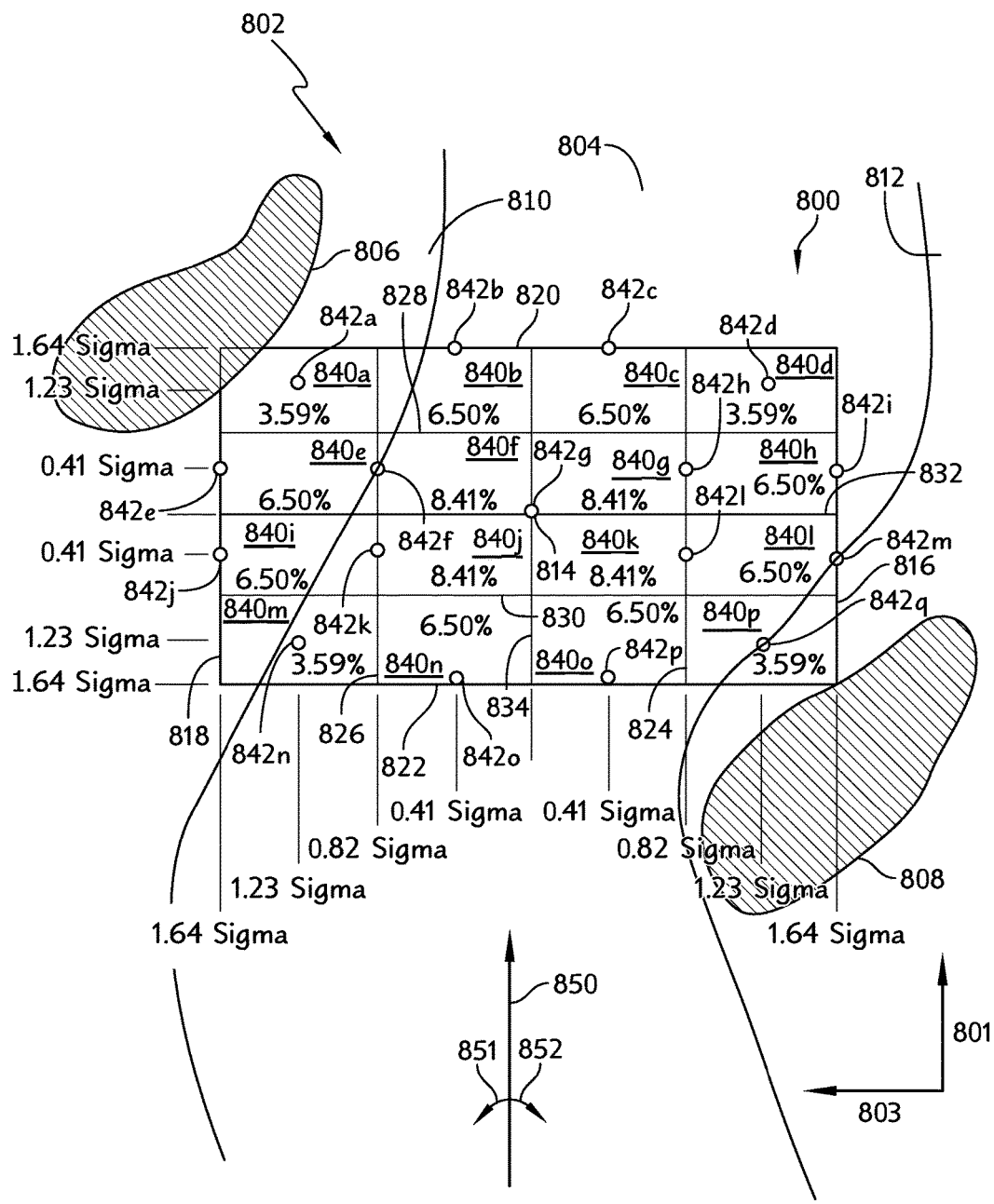
FIG. 8 illustrates a method for computing two dimensional statistics regarding likelihoods of landing locations for a golf shot, in accordance with the present disclosure.

FIG. 8 illustrates an alternative method for computing two dimensional statistics regarding statistical likelihoods of the golf ball 103 landing in particular locations. FIG. 8 shows a grid 800 that would be stored in programmatic form by the software application 104. The grid 800 includes sixteen box regions 840a-840p, each of which represents a geographical region of a portion of a hole of a golf course. This is depicted in FIG. 8 by overlaying the grid 800 on a graphical representation of a portion of a hole 802. In this example, the hole 802 includes a fairway 804, a first bunker 806, a second bunker 808, a left rough 810, and a right rough 812.

Generally, for a given golf club type, the golfer 101 will have a mean and a standard deviation for the distance with which the golfer 101 can hit the golf ball 103, and a mean and a standard deviation for the direction in which the golfer 101 actually hits the golf ball 103 when aiming in a particular direction. Shown in FIG. 8 is a distance axis 801 and a direction axis 803. The mean and standard deviation for a golf shot by the golfer 101 along both the distance axis 801 and the direction axis 803 can be computed based on statistics stored in the database 155, as explained in connection with FIG. 2.

The software application 104 centers the grid 800 at a mean location 814 representing the location at which the golf ball 103 would land if the golfer 101 hit the golf ball 103 a mean distance and in a mean direction. The software application then extends a mean boundary line 832 along the direction axis 803, and extends a mean boundary line 834 along the distance axis 801.

In this illustrative embodiment, the software application 104 creates a right boundary line 816 and a left boundary line 818 at locations 1.64 standard deviations (with reference to the direction statistics for the golfer 101) away from the mean location 814 along the direction axis 803. The software application 104 creates a top boundary line 820 and a bottom boundary line 822 at locations 1.64 standard deviations (with reference to the distance statistics for the golfer 101) away from the mean location 814 along the distance axis 801. Although other standard deviation multiples can be chosen, 1.64 standard deviations was selected for this illustrative embodiment because, for normal distributions, it is generally understood that outcomes within 1.64 standard deviations of the mean are 90% likely to occur. Thus, the grid 800 approximates a region of the hole 802 in which the golf ball 103 has approximately a 90% chance of landing.

The software application 104 then creates intermediate boundary lines 824 and 826 at locations along the direction axis 803 that are half way between the mean boundary line 834 and the right boundary line 816/left boundary line 818, respectively (i.e., 0.82 standard deviations from the mean direction for the golfer 101 on either side). Similarly, the software application 104 creates intermediate boundary lines 828 and 830 at locations along the distance axis 801 that are half way between the mean boundary line 832 and the top boundary line 820/bottom boundary line 822, respectively (i.e., 0.82 standard deviations from the mean distance for the golfer 101).

The software application 104 then computes the statistical likelihood of the golf ball 103 landing in each of the box regions 840a-840p defined by the boundary lines described above. In this illustrative example, the statistical likelihood of the golf ball 103 landing in each of the box regions 840f, 840g, 840j, and 804k was computed as 8.41%. This is because it is generally understood that, for a normal distribution, outcomes within 0.82 standard deviations have approximately a 29% statistical likelihood. Box regions 840f, 840g, 840j, and 804k are each defined by boundaries that are 0.82 standard deviations away from the mean along both the distance axis 802 and the direction axis 803. Thus, a 29% statistical likelihood along both the distance axis 801 and the direction axis 803 amounts to an approximate statistical likelihood of 8.41% (29%×29%).

Box regions 840h, 840l, 840e, and 840i are between 0.82 and 1.64 standard deviations away from the mean with respect to the direction axis 803 and within 0.82 standard deviations away from the mean with respect to the distance axis 801. It is generally understood that, for a normal distribution, the statistical likelihood of an occurrence falling between 0.82 standard deviations and 1.64 standard deviations is approximately 16%. Thus, each of the box regions 840h, 840l, 840e, and 840i would be assigned a statistical likelihood of 4.64% (29%×16%). (Note that a different likelihood is shown in FIG. 8 for reasons that will be explained shortly.) The same applies to box regions 840b, 840c, 840n, and 840o, which are between 0.82 standard deviations and 1.64 standard deviations away from the mean with respect to the distance axis 801 and within 0.82 standard deviations away from the mean with respect to the direction axis 803—i.e., they would each be assigned a statistical likelihood of 4.64%. Box regions 840a, 840d, 840m, and 840p are between 0.82 standard deviations and 1.64 standard deviations away from the mean with respect to both the direction axis 803 and the distance axis 801, and thus would be assigned statistical likelihoods of 2.56% (16%×16%).

However, in this illustrative embodiment, the statistical likelihoods for box regions 840a-d, 840e, 840h, 840i, 840l, and 840m-p have been scaled by a factor of 1.401 so that the statistical likelihoods shown within grid 800 add up to 100%. In this respect, the statistical likelihoods shown within grid 800 are an approximation formed by adding the statistical likelihood that the golf ball 103 will land outside the grid 800 to the statistical likelihoods that the golf ball 103 will land in one of the box regions 840a-d, 840e, 840h, 840i, 840l, and 840m-p on the periphery of the grid 800. Thus, box regions 840h, 840l, 840e, 840i, 840b, 840c, 840n, and 840o are assigned statistical likelihoods of 6.5%, and box regions 840a, 840d, 840m, and 840p are assigned statistical likelihoods of 3.59%.

The statistical approximations shown within the grid 800 can be generated according to other methodologies, such as by increasing the resolution of the grid 800 (i.e., forming additional box regions by selecting smaller standard deviation multiples with which to create boundary lines), by assuming the statistical distribution governing the golf shots by the golfer 101 is something other than a normal distribution, or the like.

As will be explained in more detail in connection with FIG. 9, for computational reasons it may be advantageous for the software application 104 to compute statistical likelihoods that the golf ball 103 will land in particular representative locations rather than within one of the box regions 840a-p. Thus, FIG. 8 shows representative locations 842a-842q within the grid 800. In this illustrative embodiment, statistical likelihoods for the representative locations 842f, 842g, 842h, 842k, and 842l are estimated as collectively accounting for the statistical likelihoods of box regions 840f, 840g, 840j, and 840k, and are thus assigned statistical likelihoods of 6.728% (8.41%×4/5). Representative locations 842a, 842d, 842n, and 842q are assigned statistical likelihoods equal to statistical likelihoods for the box regions in which they lie, or 3.59%. All other representative locations 842b, 842c, 842e, 842i, 842j, 842m, 842o, and 842p are assigned statistical likelihoods of 6.5%, equal to respective box regions nearest to the representative locations. Of course, other methods for selecting the placement and number of representative locations and/or for assigning statistical likelihoods are within the scope of the present disclosure.

Thus, the description above in connection with FIGS. 7-8 explain how to compute the statistical likelihood of the golf ball 103 landing in a particular region or a particular representative location when the golfer 101 uses a particular golf club type for which the database 155 includes statistics on past performances of the golfer 101 with respect to distance and direction. The software application 104 then uses the statistics computed according to these methodologies in order to recommend a golf club type and target directional line for the golfer 101. According to certain illustrative embodiments, the software application 104 may use a methodology that takes into account three cases:

Case 1: Golf Shot from Tee Box on a Par 4 or Par 5 Hole:

The software application 104 begins by assessing statistical likelihoods assuming that the golfer 101 uses a golf shot with a golf club type of "driver" and a target directional line 850 towards the middle of the fairway 804. If the statistical likelihood of the golf ball 103 landing in a hazard, such as the first or second bunkers 806 or 808, or in other hazards not shown (e.g., other bunkers, water hazards, tree hazards, etc.) is higher on one side of the mean boundary line 834 with respect to direction axis 803 than the other, the software application 104 will select an alternative target directional line 850 (e.g., by rotating in either direction 851 or direction 852), and will continue selecting successive alternative target directional lines 850 until the statistical likelihood of the golf ball 103 landing in a hazard is 0, or is an equal percentage on both sides of mean boundary line 834 with respect to the direction axis 803.

The software application 104 then computes a statistically probable score for the remainder of the hole 802, according to a methodology that will be discussed in connection with FIG. 9.

The software application 104 then iterates to a subsequent golf club type having a lower statistical variance—e.g., after a driver, the software application may iterate to a 3-wood. The software application adjusts the target directional line 850 in the same manner as explained above, and then re-computes a statistically probable score for the remainder of the hole 802, according to a methodology that will be discussed in connection with FIG. 9.

In certain embodiments, the software application 104 continues iterating among golf club types so long as the statistically probable score for that golf club type is lower than that computed by the previous iteration. The software application 104 then terminates its iterations and determines that the golf club type on which it terminated should be the statistically recommended golf club type. In other embodiments, the software application 104 continues iterating among golf club types until it encounters a golf club type where the statistical likelihood of the golf ball 103 landing in a hazard is 0, and then selects that golf club type as the statistically preferred golf club type as long as its statistically probable score is lower than previous golf club types through which the software application 104 iterated.

In certain embodiments, to save computational burden, the software application 104 does not undertake to perform computations for golf club types not typically suitable for golf shots from a tee box on a par 4 or 5, such as short irons. In certain embodiments, the golfer 101 can select settings in software application 104 that specify the golf club types the golfer 101 wants considered for golf shots from a tee box.

Case 2: Golf Shot on a Second or Subsequent Shot, Other than Shots for which the Golfer 101 Seeks to Reach the Green:

The software application 104 implements a similar methodology as that described for Case 1 above, but in certain embodiments, the software application 104 eliminates the driver from the golf club types through which it iterates in order to lower computational burden. In certain embodiments, the golfer 101 can select settings in the software application 104 that specify the golf club types the golfer 101 wants considered for this Case (or for any of the other Cases).

Case 3: Golf Shots where the Golfer 101 Seeks to Reach the Green (not Shown in FIG. 8)

The software application 104 begins with a golf club type for which the mean location 814 is shortest along direction axis 801 while still being located past the physical hole (not shown in FIG. 8) of the green (not shown in FIG. 8). For the purpose of discussing this case, the golf club type meeting this criteria will be referred to as the "first candidate golf club type." The software application selects a target directional line 850 directed towards the location of a physical hole for the hole 802. In certain embodiments, if the statistical likelihood of the golf ball 103 landing in a hazard is higher on one side of the mean boundary line 834 with respect to direction axis 803 than the other, the software application 104 selects an alternative target directional line 850 (e.g., by rotating in either direction 851 or direction 852) and continues selecting successive alternative target directional lines 850 until the statistical likelihood of the golf ball 103 landing in a hazard is 0, or is an equal percentage on both sides of mean boundary line 834 with respect to axis 803. In certain embodiments, if the statistical likelihood of the golf ball 103 landing in a rough 810 or 812 is higher on one side of the mean boundary line 834 with respect to direction axis 803 than the other, the software application 104 selects an alternative target directional line 850 (e.g., by rotating in either direction 851 or direction 852) and continues selecting successive alternative target directional lines 850 until the statistical likelihood of the golf ball 103 landing in a rough 810 or 812 is 0, or is an equal percentage on both sides of mean boundary line 834 with respect to axis 803. In certain embodiments, the software application 104 adjusts the directional orientation 150 to equalize or eliminate the likelihood of the golf ball 103 landing in a hazard, and then adjusts the directional orientation 150 to equalize or eliminate the likelihood of the golf ball 103 landing in a rough. In still other embodiments, the software application 104 adjusts the directional orientation 150 to equalize or eliminate the likelihood of the golf ball 103 landing in a rough, and then adjusts the directional orientation 150 to equalize or eliminate the likelihood of the golf ball 103 landing in a hazard.

The software application 104 next proceeds to analyze the golf club type for which the mean location 814 is next shortest along the distance axis 801—i.e., the golf club type for which the mean location 814 is farthest along direction axis 801 while being located short of the physical hole (not shown in FIG. 8) of the green (not shown in FIG. 8). For the purpose of discussing this case, the golf club type meeting this criteria will be referred to as the "second candidate golf club type." The software application 104 adjusts the directional orientation 150 for the second candidate golf club type in a similar manner as for the first candidate golf club type.

The software application 104 then computes a statistically probable score for the first candidate golf club type and the second candidate golf club type using a methodology that will be discussed in connection with FIG. 9, and selects the golf club type having the lower statistically probable score as the recommended golf club type.

Case 4: Golf Shots Taken from on or Near the Green (not Shown in FIG. 8)

For golf shots taken from on or near the green, the software application 104 may not compute any statistical likelihoods, as the golf club type that the golfer 101 should use may be apparent—e.g., a putter. However, for computational reasons that will be explained in connection with FIG. 9, the software application 104 may nonetheless want to obtain information on a statistically expected number of strokes to complete the hole for the golfer 101 from locations on or near the green. For this, the software application 104 may use already-provided "short game" data. This will be explained in more detail in connection with FIG. 9.

Figure 9:
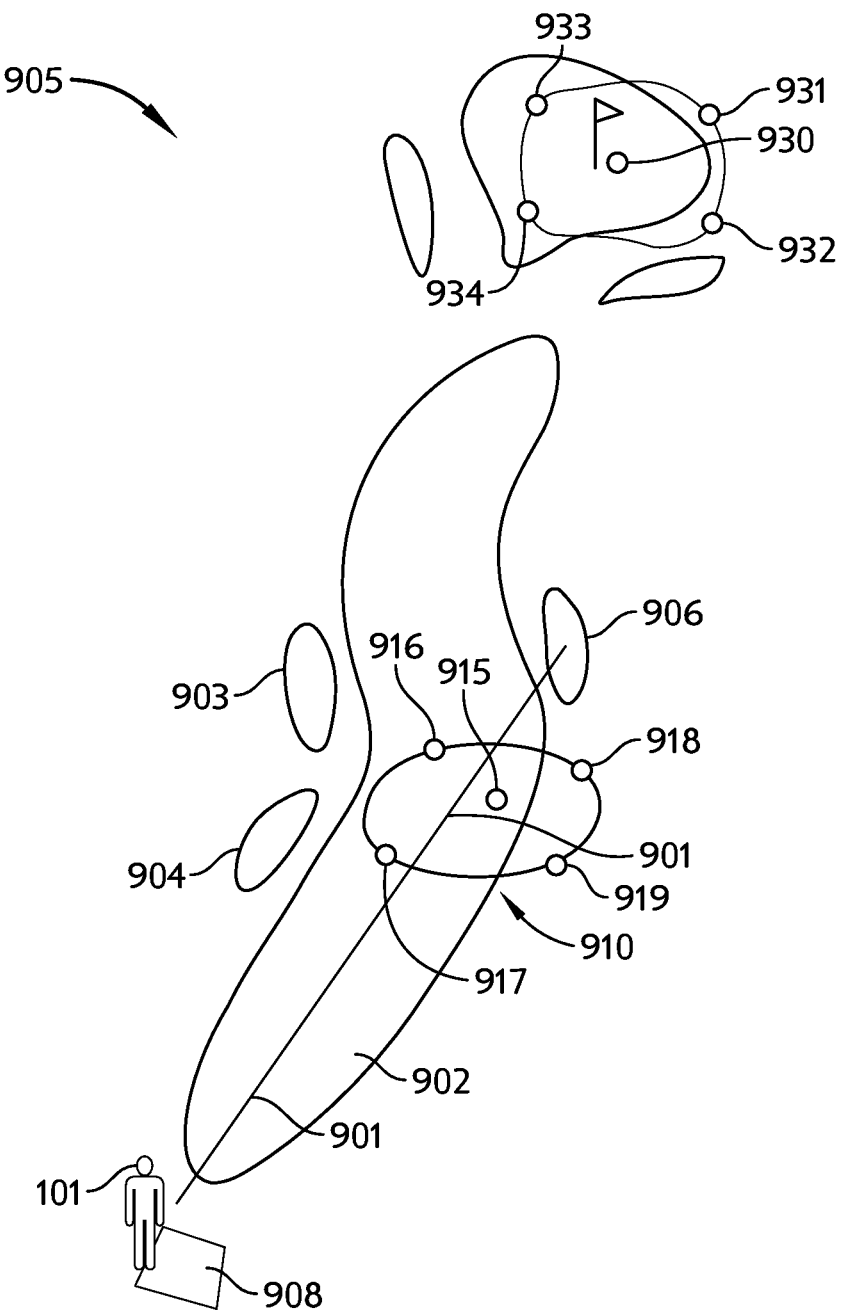
FIG. 9 is a diagram depicting the manner by which an exemplary system iteratively computes statistically probable scores for a hole, in accordance with the present disclosure.

FIG. 9 is a diagram depicting the manner by which an exemplary system iteratively computes statistically probable scores for a hole. FIG. 9 shows a hole 905, with the golfer 101 at a location 908. In this illustrative embodiment, the software system 104 is determining statistical likelihoods and a statistically probable score associated with the use of a 3 wood by the golfer 101 from the location 908 using a target directional line 901 to the right side of the fairway 902, as to avoid the first and second sand traps 903 and 904 to the left of the fairway 902 and the sand trap 906 on the right of the fairway 902. After performing computations associated with the use of a 3 wood, the software application 104 will iterate through other golf club types to identify a recommended golf club type.

Using the methodologies discussed above in connection with FIGS. 7-8, the software system 104 can compute statistical likelihoods of that the golf ball 103 will land in various locations on the hole 905. In this illustrative embodiment, the software system 104 identifies a region 910 having representative locations 915-919 for which statistical likelihoods can be assigned using methodologies discussed above in connection with FIG. 8. Whereas FIG. 8 showed seventeen representative locations 842a-842p, FIG. 9 shows five representative locations 915-919 for ease of explanation.

The software system 104 then performs "next shot scenario" analysis. In performing next shot scenario analysis, the software system 104 begins with one of the representative locations 915-919. In this illustrative example, the software system 104 begins with the representative location 915 to analyze a "next shot"—i.e., a shot that the golfer 101 would take if his current shot landed at the location 915. Thus, the software application 104 considers the hypothetical scenario in which the golfer 101 is at the representative location 915.

For the "next shot" analysis from representative location 915, the software application 104 begins with a given golf club type to analyze—in this example, it begins with a 3 iron—and determines the statistically probable score for the golfer 101 from the representative location 915 using the 3 iron. To do so, the software application 104 considers representative locations 930-934 that could result from a golf shot from representative location 915. The software application 104 computes statistical likelihoods for the golf ball 103 landing in the representative locations 930-934 using the 3 iron using the methodologies described above in connection with FIG. 8. The software application 104 computes a statistically expected number of shots to complete the hole 905 from the representative location 915 using a 3 iron by computing a weighted sum of the statistically expected number of shots to complete the hole 905 from each of the representative locations 930-934, each being weighted by the respective statistical likelihoods of the golf ball 103 landing in each of the representative locations 930-934.

To do this, the software application obtains data regarding the expected number of shots to complete the hole 905 from each of the representative locations 930-934. In this regard, the software application 104 and/or the database 155 may be pre-programmed with statistically expected number of shots for the golfer 101 to complete the hole 905 from each of the representative locations 930-934 and/or the software application 104 may make assumptions regarding the statistically expected number of shots for the golfer 101 to complete the hole 905 from each of the representative locations 930-934. For example, "short game" data could be used to calculate the total amount of strokes from representative locations 930-934. As examples, prior data on statistically expected numbers of shots may exist for greenside bunker shots, greenside chips, putts from 30 feet or longer, putts from 15-30 feet, putts from 5-15 feet, and putts from less than 5 feet could be used for shots from those locations. The user could have the ability to load this type of data into the software application 104 and/or the database 155, or the system could be pre-programmed with such data for golfers having a similar golf handicap of the golfer 101. Many possible implementations of short game data could be used, and each could have benefits or drawbacks on accuracy, time for calculations, or general usability of the system.

In this example, the software application may assign a statistically expected number of shots equal to 1.7 for the representative locations 930, 933, and 934, as those representative locations are on the green 938 and close to the physical hole 936, and may assign a statistically expected number of shots equal to 2.8 for the representative locations 931 and 932, which are on a greenside rough.

After weighting the statistically expected number of shots to complete the hole from each of the representative locations 930-934 by the statistical likelihood that the golf shot from representative location 915 using a 3 iron will land at each of the representative locations 930-934, the software application may computed a weighted sum. This weighted sum represents the expected number of shots to complete the hole 905 with a 3 iron from the representative location 915.

The software application 104 iterates through other golf club types besides the 3 iron to identify the golf club type yielding the lowest expected number of shots to complete the hole 905 from the representative location 915. The software application 104 selects the lowest computed expected number of shots as the expected number of shots to complete the hole 905 from the representative location 915.

The software application 104 performs a similar analysis to determine the expected number of shots to complete the hole 905 from each of the representative locations 916, 917, 918, and 919.

The software application 104 then computes a statistically probable number of shots to complete the hole from the location 908 using a 3 wood, by computing a weighted sum that adds the statistically expected number of shots to complete the hole 905 from each of the representative locations 915-919, each weighted by the respective statistical likelihoods of the golf ball 103 landing in each of the representative locations 915-919.

The software application 104 then iterates through other golf club types to identify the golf club type yielding the lowest statistically probable number of shots to complete the hole from the location 908, and identifies that golf club type as the recommended golf club type.

The example depicted in connection with FIG. 9 was for a par 4 hole, but similar analysis can be performed for par 3 holes, par 5 holes, etc. The computational requirements will generally increase, as the number of representative locations to be considered will increase exponentially for a par 4 as compared to a par 3, etc. Various algorithmic techniques can be used to compute the statistically probable number of shots to complete the hole 905 in accordance with the description above, including those known in the art of dynamic programming.

Various approaches to reducing the computational demands of the methodology described above can be implemented. In certain embodiments, the software application 104 decreases the number of representative locations—e.g., by considering fewer locations than the seventeen representative locations 842a-842p depicted in connection with FIG. 8. In certain embodiments, the software application 104 consolidates certain representative locations. For example, the software application 104 could consolidate representative locations 915 and 916, as both are generally aligned with one another and are likely to lead to similar outcomes. To consolidate representative locations 915 and 916, the software application 104 may identify one or the other of the representative locations 915 and 916 (or alternatively may choose a midpoint between the representative locations 915 and 916) and may assume that its statistical likelihood is the sum of the statistical likelihoods associated with representative locations 915 and 916. A similar approach may be used to combine more than two representative locations.

In certain embodiments, the software application 104 may consolidate all representative locations within the same physical feature—e.g., all representative locations in a bunker would be consolidated into one representative location, all representative locations in a rough would be consolidated into one representative location, etc. In certain embodiments involving par 4 or par 5 holes, the software application could consider fewer numbers of representative locations for a second shot than a first, fewer numbers of representative locations for a third shot than a second, and so on. In certain embodiments, the software application 104 could include a hard limit on the amount of computational time it invests in any iteration of the above-described methodologies, and/or could include a hard limit on the number of iterations it performs for any step of the above-described methodologies. The limit on computational time could be set by the golfer 101 based on preferences of the golfer 101 on the duration of time within which he would like feedback from the software application 104. In certain embodiments, limits are imposed dependent upon the computing capabilities of the mobile computing device 102, such that higher performance mobile computing devices would have higher limits. As previously explained, there exists a tradeoff between amount of time and number of iterations allowed on the one hand and the accuracy of the calculated results on the other hand.

In certain embodiments, as explained, the software application 104 could limit the golf club types available for consideration at any given location—e.g., for par 5 holes off the tee, the software application 104 may consider only the driver and a select number of additional woods. In certain embodiments, as explained, the software application 104 could cease performing iterations in certain situations—e.g., for par 5 holes off the tee, the software application 104 could stop iterating as soon as a golf club type is identified that has a suitably low chance of resulting in the golf ball 103 landing in a hazard.

In other embodiments, the software application 104 could perform computations for holes of a golf course prior to the golfer 101 playing the holes of the golf course, thus pre-computing a course management plan. For each hole, the golfer 101 would follow the pre-computed recommendations by the software application 104 for the initial shot by the golfer 101 off of the tee. For the second and subsequent shots for each hole, the software application 104 would only need to update its pre-computed computations based on the results of the initial shots. This may save time and computational burden while the golfer 101 is on the golf course.

Figure 10A:
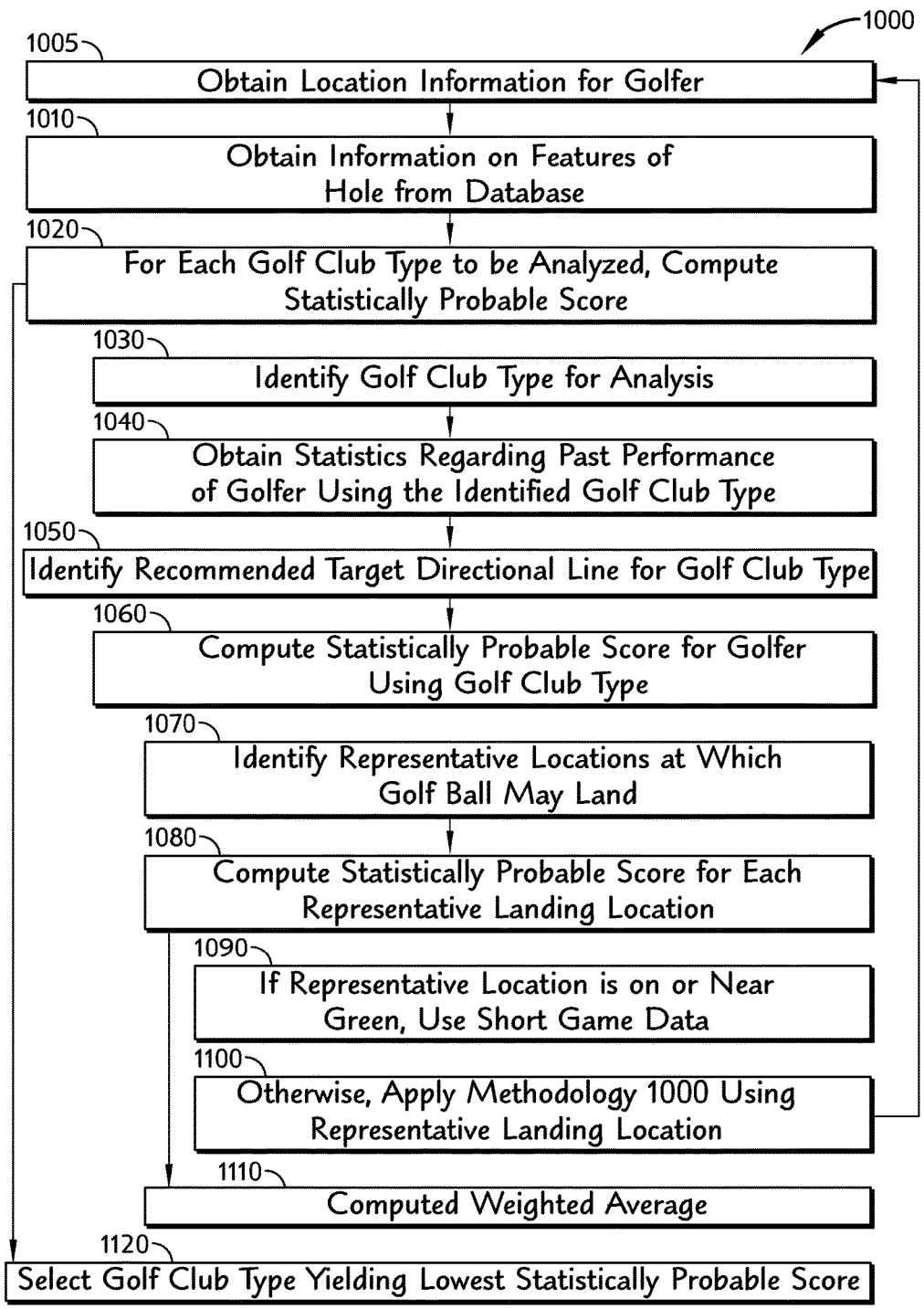
FIG. 10A is a flow diagram illustrating an exemplary method followed by a software application, in accordance with the present disclosure.

FIG. 10A is a flow diagram illustrating a method 1000 followed by a software application in accordance with the present disclosure. In step 1005, the software application 104 obtains location information for golfer, such as through a GPS module (to be discussed below). In step 1010, the software application 104 obtains information on features of a hole from the database 155, such as the location of a fairway, hazards, green, etc.

In step 1020, the software application 104 performs a sequence of steps for each golf club type to be analyzed. In step 1030, the software application selects one of the golf club types to be analyzed. In step 1040, the software application 104 obtain statistics regarding the past performances of the golfer 101 using the selected golf club type. In step 1050, the software application 104 identifies a recommended target directional line for golf club type, using techniques described above. In step 1060, the software application computes a statistically probable score for the golfer 101 using the golf club type under analysis.

To do so, the software application follows a sequence of steps. In step 1070, the software application 104 identifies representative locations at which golf ball 103 may land when the golfer 101 uses the golf club type under analysis. In step 1080, the software application computes a statistically probable score for each representative landing location. To do this, the software application 104 determines (step 1090) whether the representative locations are on or near the green, in which case the software application 104 uses available short game data. Otherwise, the software application 104 (step 1100) applies methodology 1000 to the representative landing location to determine the statistically probable score for that representative landing location.

In step 1110, the software application 104 computes a weighted average to complete the computation of the statistically probable score for the golfer 101 using the golf club type under analysis.

The step 1020 is iterated for each golf club type to be analyzed. In step 1120, the software application 104 selects the golf club type yielding lowest statistically probable score as the recommended golf club type.

Figure 10B:
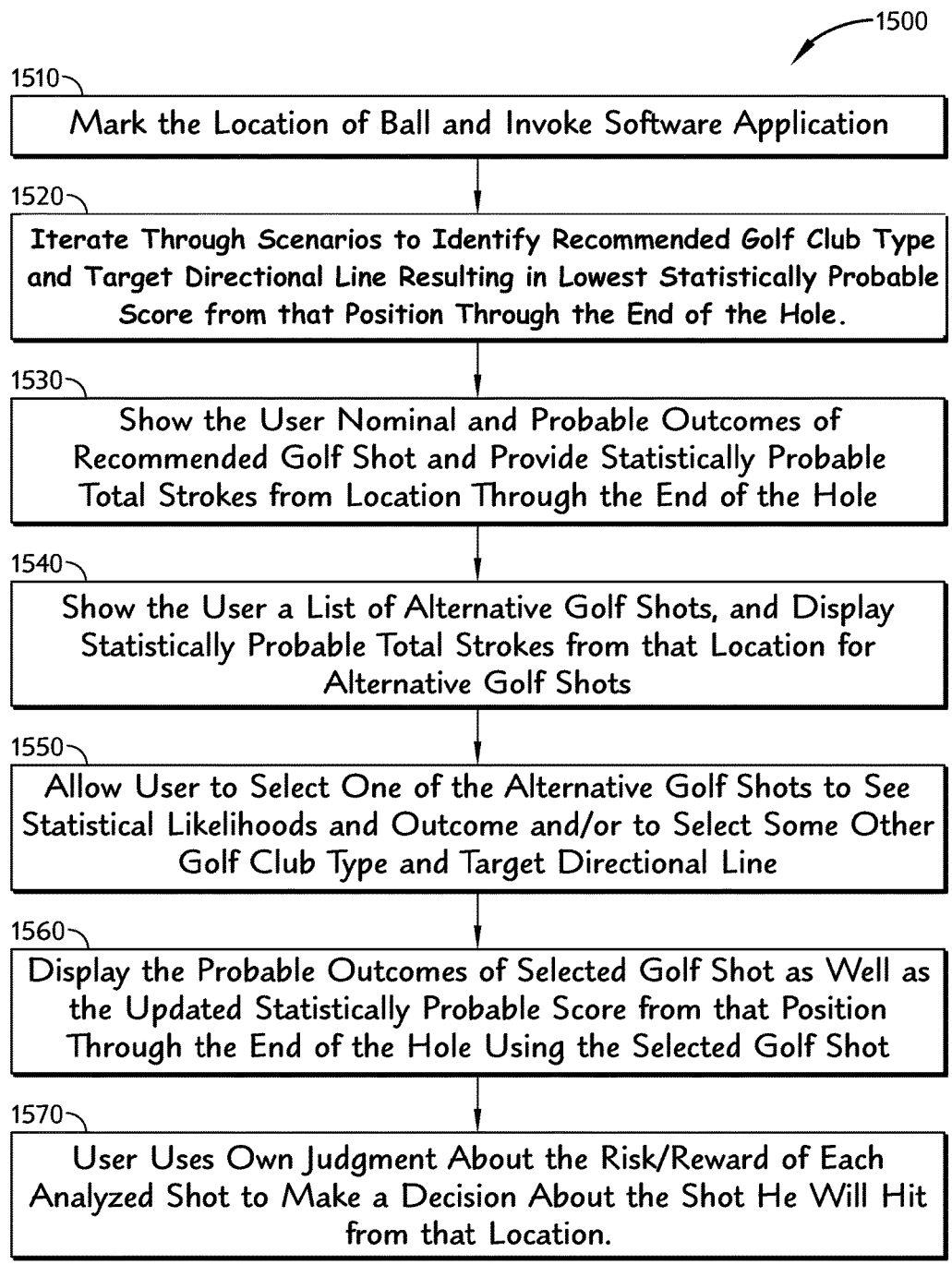
FIG. 10B is a flow diagram illustrating an exemplary method of use of a software application, in accordance with the present disclosure

FIG. 10B is a flow diagram 1500 illustrating an exemplary method of use of a software application in accordance with the present disclosure. In step 1510, the location of the ball is determined (e.g., through GPS or through physical input by the golfer 101 into the mobile computing device 102), and the software application 104 is invoked. In step 1520, the software application 104 iterates through scenarios to identify a recommended golf club type and a target directional line resulting in the lowest statistically probable score from that position through the end of the hole. In step 1530, the software application 104 shows the user a nominal (i.e., mean) and probable outcome of the recommended golf shot and provides the statistically probable total strokes from the location through the end of the hole. In step 1540, the software application 104 shows the user a list of alternative golf shots, and displays statistically probable total strokes from that location for alternative golf shots. In step 1550, the software 104 allows the user to select one of the alternative golf shots to see statistical likelihoods and outcome and/or to select some other golf club type and target directional line. In step 1560, the software application 104 displays the probable outcomes of selected golf shot as well as the updated statistically probable score from that position through the end of the hole using the selected golf shot.

Other variations are within the scope of the present disclosure. For example, as more data is gathered to determine the statistical capability of a golfer, more detailed information could be included about the course and/or the golfer's capabilities in order to provide improved information for the golfer. For example, the software application 104 could indicate areas around fairways or greens which are "bad zones". Landing in these zones would result in additional strokes as compared to the typical result of just being off the fairway or off the green. Examples of "bad zones" include high-fescue areas, severely-sloped drop-offs around the greens, false fronts to greens, extremely deep and difficult bunkers, areas around the greens where the slope of the green would be away from the golfer making the chip much more difficult, and the like.

Other examples of improved information could be taking into account adverse conditions such as cold, high wind, or difficult rough. The golfers capability could be adjusted for these situations, such as increasing standard deviations by 25% in high wind conditions, increasing standard deviations by 50% in the rough, and reducing mean distance by 10% in cold weather conditions. These types of additional factors will provide even more accurate information for the user and more accurate results when calculating the lowest statistical score for the golfer on the given hole.

Figure 11:
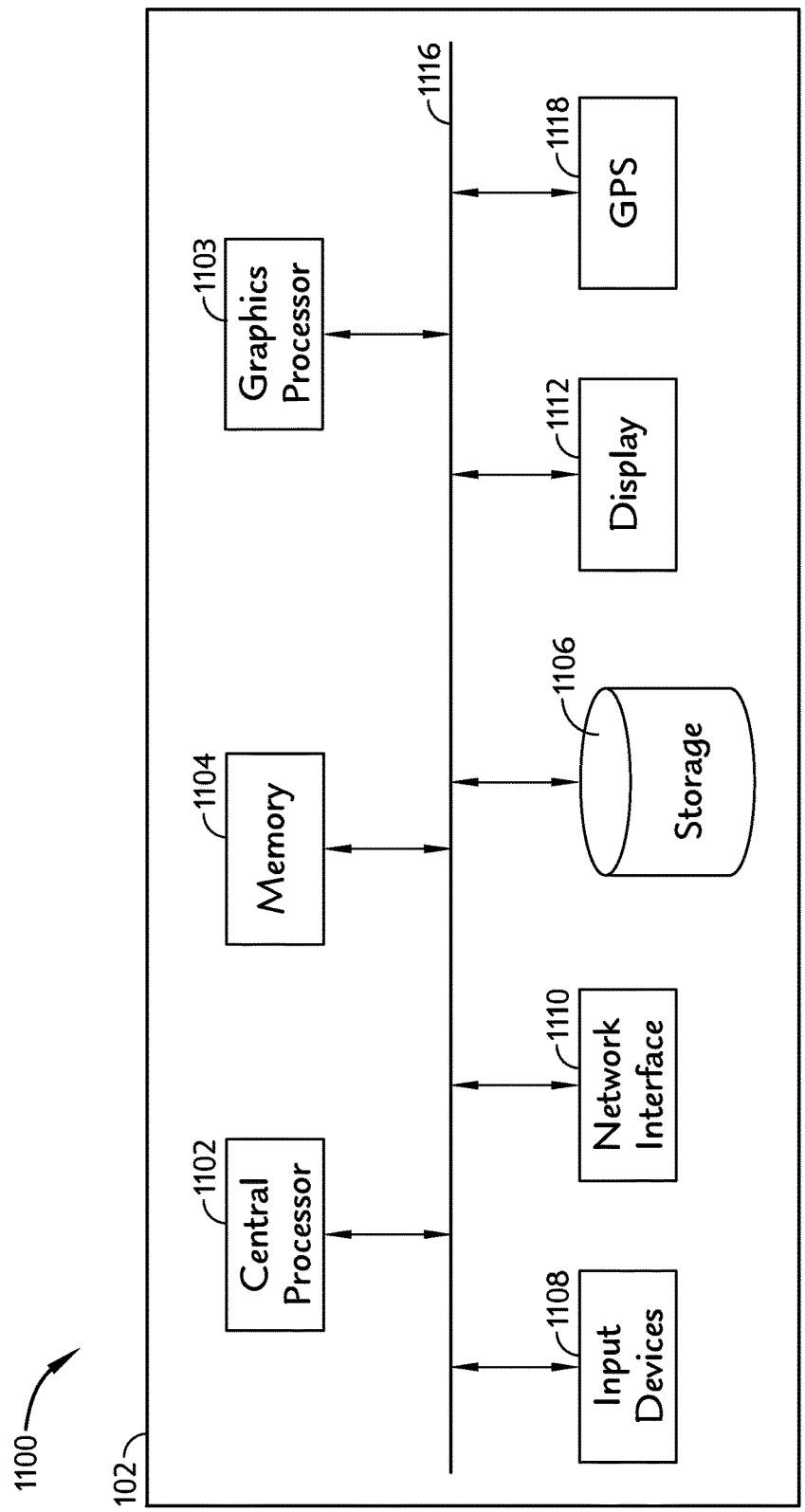
FIG. 11 is a block diagram showing the hardware components of an exemplary mobile device that contains software for aiding the selection of a golf shot, in accordance with the present disclosure.

FIG. 11 is a block diagram 1100 showing the hardware and software components of an exemplary mobile device 102 that contains the software system 104 for aiding the selection of a golf shot. The mobile device 102 includes a central processor 1102, a graphics processor 1103, a memory 1104, a storage 1106, input devices 1108, a network interface 1110, a display 1112, and a GPS module 1118. The system components may be in communication via an interconnect bus 1116.

Central processor 1102 may be from microprocessor series such as Intel Pentium, Intel Core, Intel Core 2, Intel Xeon, AMD Athlon, AMD Phenom, IBM Power, IBM PowerPC, or other such microprocessor series. Processor 202 may include a single microprocessor or a plurality of microprocessors for configuring system 200 as a multi-processor system.

The mobile device may include a specialized graphics processor 1103 to facilitate the output of images to the display 1112. Exemplary graphics processors include those available from Intel or Nvidia. In other embodiments, the central processor 1102 handles graphics processing functionality and a separate graphics processor 1103 is not provided.

Memory 1104 may include read-only (ROM) or random access (RAM) memories, such as a synchronous dynamic random access memory (SDRAM), capable of storing data as well as instructions to be executed by central processor 1102 and/or graphics processor 1103. Storage 1106 may include a hard disk drive (HDD), a flash drive, or other suitable computer readable media, for storing data and instructions for use by the central processor 1102. Input devices 1108 may include any input device suitable for a mobile computing device, such as a touchscreen display, a keyboard (e.g., a slideout keyboard), a stylus, a trackball, or other suitable devices. Network interface 1110 may include a network card and/or any other suitable data communications components and circuitry for communicating with one or more remote systems. For example, network interface 1110 may provide 802.11 ("WiFi") connectivity, cellular network connectivity, Bluetooth connectivity, and the like. Display 1112 may include one or more liquid crystal display (LCD) displays, OLED displays, or other suitable display type. As explained, the display 1112 may be touch- or stylus-sensitive. GPS module 1118 is any suitable component that allows for tracking the geolocation of the mobile computing device 102.

The mobile computing device 102 also includes an operating system which, as discussed above, may be selected from among Apple's iOS line of operating systems, the Android line of operating systems, the Windows Mobile or Windows Phone line of operating systems, or BlackBerry operating systems. The mobile computing device 102 also includes software applications, of which the software application 104 is one. The software applications 1122 may be implemented using any known programming languages, including by way of example C, C++, C#, or Java. The operating system may expose certain Application Programming Interface (API) functionality by which software applications 1122, including software application 104, may access underlying hardware functionality of the mobile computing device 102, such as the ability to transmit data to and receive data from a network using network interface 1110, the ability to write data to and read data from the storage 1106 and memory 1104, the ability to write data to the display 1112 (e.g., a frame buffer) and receive information regarding user touchscreen or stylus-driven inputs from display 1112, the ability to receive information regarding user inputs from the input devices 1108, the ability to obtain geolocation information from the GPS module 1118, and the ability to cause execution of compiled program code by the central processor 1102 and/or the graphics processor 1103.

While the description above was made in connection with mobile computing device 102, the foregoing disclosures could likewise be implemented on a non-mobile computing system, such as a personal computer or a workstation. A personal computer or workstation may be provide the benefit of enhanced computational power. Thus, the software system 104 may be provided on a personal computer or workstation running a Windows-based operating system, a personal computer or workstation from Apple, a personal computer or workstation running UNIX, a personal computer or workstation running Linux, or any other suitable platform.

Though not depicted by way of a figure, it should be understood that the database server 150 will also include components common to computer servers, including a central processor (e.g., from Intel or AMD), storage (e.g., a hard disk drive, flash drive, etc.), a memory (e.g., ROM or RAM), input devices (e.g., keyboard, mouse, etc.), a network interface (e.g., 802.11 "WiFi" connectivity, Ethernet connectivity, etc.), and a display (e.g., monitor). As explained, database server 150 and database 155 may be implemented using any known database environment, such as Oracle, DB2, or SQL Server. Database 155 may be a relational database.

The computations above were disclosed to have been performed on mobile computing device 104. However, computations may be off-loaded to a separate computational server not shown in the Figures.

While this invention has been described in conjunction with the specific embodiments outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

Although certain illustrative embodiments have been described in detail above, variations and modifications exist within the scope and spirit of this disclosure as described and as defined in the claims included in this application.

We claim:

1. A computer implemented method comprising:
   determining, by a computing device, a position of the computing device based upon data from a sensor in the computing device;
   querying, by the computing device, a storage device for information regarding geographical area of a golf course, where the computing device is located, and locations of holes, fairways, greens, bunkers, hazards, and roughs;
   displaying, by the computing device, the position of the computing device with respect to the geographical area on the golf course;
   querying, by the computing device, the storage device for information regarding statistics indicative of past performances by a user relating to distance, distance variance, and directional variance for each of a plurality of golf club types used by the user;
   determining, by the computing device, which one of the plurality of golf club types the user should use based upon retrieved statistics of the past performance of the user with all of the plurality of golf club types in view of a location of the computing device with respect to the location of a hole, fairways, greens, bunkers, hazards, roughs of the geographical area by calculating the probabilities of a golf shot by the user landing in various possible locations on the golf course given the statistical performance characteristics of the user with a golf club type;
   determining, by the computing device, a recommended distance and target line for the user based upon the statistical performance characteristics of the user relating to distance, distance variance, and directional variance for a selected club type in view of the position of the computing device on the golf course with respect to the location of the hole, fairways, greens, bunkers, hazards, roughs of the geographical area by evaluating the current golf shot options of the user and then successive golf shot options from the statistically probable resulting landing locations from original shot options until an original shot option is calculated to give the user the lowest statistical score on the hole given the own statistical performance characteristics of the user; and
   displaying by the computing device the statistically preferred golf club type and target line to the user and graphically illustrating a preferred distance and target line for the user.

2. The method of claim 1, further comprising collecting the statistics indicative of past performances in a database upon a golfer using the plurality of golf club types at locations different from the golf course.

3. The method of claim 2, wherein the statistics indicative of past performances include information on mean golf ball travel distance, information on variance of golf ball travel distance, information on mean golf ball directional orientation, and information on variance of golf ball directional orientation.

4. The method of claim 1, further comprising analyzing the retrieved statistics about a given golf club type by
   identifying a current location and candidate landing locations on the golf course;
   generating a statistical distribution based on mean and variance information for the given golf club type;
   displaying on the computing device the statistical distribution on a programmatic representation of a hole of the golf course; and
   determining, for each of the candidate landing locations, a respective likelihood that a golf shot will result in a golf ball landing in one of the candidate landing location.

5. The method of claim 4, further comprising, for each of the candidate landing locations for which a likelihood was determined
   identifying a subsequent set of candidate landing locations for a subsequent golf shot;
   determining a subsequent set of respective likelihoods that the subsequent golf shot will result in the golf ball landing in each of the subsequent set of candidate landing locations; and
   taking into account the subsequent set of respective likelihoods in selecting one of the plurality of golf club types as the statistically preferred golf club type.

6. The method of claim 4, further comprising
   from the current location, iteratively repeating the steps of
      identifying the current location on the golf course,
      identifying a set of the candidate landing locations on the golf course, and
      determining, for each of the candidate landing locations, the respective likelihood that the golf shot will result in the golf ball landing in that candidate landing location;
   wherein for each iteration, the current location on the golf course is taken to be one of the candidate landing locations of a prior iteration.

7. The method of claim 1, further comprising selecting one of the plurality of golf club types as the statistically preferred golf club type for the golf shot by
   calculating, for each of the plurality of golf club types, a respective expected score for the hole;
   comparing the calculated expected scores; and
   selecting the golf club type having a lowest expected score for the hole.

8. The method of claim 7, further comprising
   determining a preferred directional line for the golf shot; and
   visually identifying a line of aim, which will result in the golf shot most closely following the preferred directional line, wherein the line of aim is determined by considering an amount of draw or slice the user imparts on the shot based on the retrieved statistics of the user for a given golf club type.

9. The method of claim 1, further comprising
   displaying a graphical representation of the golf course;
   displaying a boundary of a geographic region on the graphical representation of the golf course; and
   displaying a likelihood that the golf shot will result in a golfer's golf ball of a golfer landing in the geographic region.

10. The method of claim 9, further comprising displaying multiple boundaries and displaying multiple respective likelihoods associated with the boundaries.

11. The method of claim 9, wherein the boundary corresponds to a physical feature of the hole, wherein the physical feature is one of a green, a bunker, a fairway, a rough, and a hazard.

12. The method of claim 1, further comprising
providing an indication of an alternative golf club type for use on the golf shot;
allowing a golfer to select the alternative golf club type;
analyzing statistics indicative of past performances by the golfer with the alternative golf club type;
determining likely outcomes for the golf shot based on the alternative golf club type; and
providing an expected score for the hole for the alternative golf club type.

* * * * *